United States Patent
Kim et al.

(10) Patent No.: US 12,211,207 B2
(45) Date of Patent: Jan. 28, 2025

(54) APPARATUS FOR DETERMINING DEFECTIVE HAIR FOLLICLES AND APPARATUS FOR AUTOMATICALLY SEPARATING HAIR FOLLICLES INCLUDING THE SAME

(71) Applicant: AFS INC., Seoul (KR)

(72) Inventors: Tae Hee Kim, Seoul (KR); Kyoung Ku Lee, Seoul (KR)

(73) Assignee: AFS INC., Seoul (KR)

( * ) Notice: Subject to any disclaimer, the term of this patent is extended or adjusted under 35 U.S.C. 154(b) by 779 days.

(21) Appl. No.: 17/394,657

(22) Filed: Aug. 5, 2021

(65) Prior Publication Data

US 2023/0044177 A1    Feb. 9, 2023

(51) Int. Cl.
| | |
|---|---|
| *G06T 7/00* | (2017.01) |
| *G06F 16/55* | (2019.01) |
| *G06T 7/13* | (2017.01) |
| *G06T 7/136* | (2017.01) |
| *A61B 17/00* | (2006.01) |

(52) U.S. Cl.
CPC ............ *G06T 7/0014* (2013.01); *G06F 16/55* (2019.01); *G06T 7/13* (2017.01); *G06T 7/136* (2017.01); *A61B 2017/00752* (2013.01); *G06T 2207/30242* (2013.01)

(58) Field of Classification Search
USPC ................................................ 382/128, 305
See application file for complete search history.

(56) References Cited

U.S. PATENT DOCUMENTS

| | | | |
|---|---|---|---|
| 7,627,157 B2 * | 12/2009 | Qureshi | G06T 7/0012 382/128 |
| 11,612,411 B2 * | 3/2023 | Kim | A61L 27/3604 606/133 |

(Continued)

FOREIGN PATENT DOCUMENTS

| | | | |
|---|---|---|---|
| KR | 10-2004-0048668 A | | 6/2004 |
| KR | 10-2009-0030341 A | | 3/2009 |

(Continued)

OTHER PUBLICATIONS

Korean Office Action dated May 25, 2021 for Korean Patent Application No. 10-2019-0010463.

*Primary Examiner* — Ishrat I Sherali
(74) *Attorney, Agent, or Firm* — Hauptman Ham, LLP

(57) ABSTRACT

An apparatus for determining defective hair follicles includes an image acquiring unit for acquiring an image of a follicle and a hair for each follicle separated from a scalp of an alopecic patient in an incisional hair transplant or each follicle directly extracted from an alopecic patient in a non-incisional hair transplant, an image processing unit for extracting an outline pattern of the image of the follicle and the hair by performing a contour detection process or an edge detection process on the image, a follicle shape database for storing hair pixel patterns related to various shapes of hairs and follicle pixel patterns related to various shapes of follicles, and a follicle determining unit for determining whether a follicle is normal follicle or defective follicle by comparing the outline pattern of the image with the hair pixel patterns and follicle pixel patterns stored in the follicle shape database.

17 Claims, 23 Drawing Sheets

(56) References Cited

U.S. PATENT DOCUMENTS

| | | | | |
|---|---|---|---|---|
| 2009/0080733 A1* | 3/2009 | Qureshi | ............... | G06V 20/69 |
| | | | | 382/128 |
| 2014/0261467 A1* | 9/2014 | Zhang | ................. | G06T 7/0012 |
| | | | | 703/11 |
| 2020/0000964 A1* | 1/2020 | Kim | .................. | A61L 27/3691 |

FOREIGN PATENT DOCUMENTS

| KR | 10-1800365 B1 | 11/2017 |
|---|---|---|
| KR | 10-2020-0093243 A | 8/2020 |

\* cited by examiner

Cut Area

APPARATUS FOR DETERMINING DEFECTIVE HAIR FOLLICLES AND APPARATUS FOR AUTOMATICALLY SEPARATING HAIR FOLLICLES INCLUDING THE SAME

This invention has been published as Korean Patent Laid-Open Publication No. 10-2020-0093243 on Aug. 5, 2020.

BACKGROUND

1. Field

The present invention relates to an apparatus for determining defective hair follicles and an apparatus for automatically separating hair follicles including the same.

2. Description of the Related Art

As the human body ages, hair loss (alopecia) may be experienced, wherein hair falls out from the scalp, for various reasons such as physical changes, genetic effects, hormone effects, eating habits, stress, irregular lifestyles, and environmental factors. Alopecia patients account for about 20% to 30% of the world's population, and the percentage continues to increase.

Especially in modern society where great importance is attached to beauty, the quantity of hair has a lot of influence on appearance. In general, when hair loss occurs, self-confidence decreases and may be the cause of stress such as appearing older than the person's age. Thus, according to the stage of hair loss, various types of hair loss management methods have been proposed, such as scalp management, hair loss shampoo, drug treatment, and self-hair transplants.

In self-hair transplants, since follicles without hair loss genes are taken from the back of the head, hair loss is permanently prevented and the effect is visible to the naked eye within a short period of time. Recently, hair transplants for young people have also been on the rise for beauty purposes, to look younger and boost self-confidence or to organize the forehead hairline.

Such self-hair transplants can be divided into an incisional hair transplant method that removes a portion of the patient's own scalp and a non-incisional hair transplant method that extracts only follicles one by one.

In the incisional hair transplants, several follicle separating professionals separate the follicles one by one after cutting and removing a portion of the scalp, which takes a long time and the speed of separating hair follicles varies greatly depending on the skill of the worker. In addition, there are problems such as irregular separation of follicles, varying quality of follicle separation even if a same worker does the job depending on the worker's condition that day, long operation time which makes the patient feels uncomfortable and increases operation costs due to the labor costs of the follicle separating professional.

In the non-incisional hair transplants, follicles are extracted and then the connective tissue of the extracted follicles need cutting and trimming so that they can be easily planted on the scalp. Accordingly, there are problems where the fatigue level of both doctor and patient increases, and as the concentration of the doctor decreases due to the accumulation of fatigue, this causes damage to healthy follicles such as cutting the same when collecting the follicles, which lowers engraftment rate.

To cope with these problems, for example, in Korean Patent No. 10-1800365, an apparatus for automatically separating follicles in an incisional hair transplant or in a non-incisional hair transplant.

When extracting follicles from a scalp in the incisional or non-incisional hair transplants, some follicles may be damaged. As damaged follicles show remarkably low survival rate, it is necessary to selectively remove the damaged follicles before a hair transplant.

SUMMARY

According to some embodiments of the present invention, an apparatus for determining defective hair follicles includes an image acquiring unit configured to acquire an image of a follicle and a hair included in the follicle for each follicle separated from a scalp cut from back of a head of an alopecic patient in an incisional hair transplant or each follicle directly extracted from back of a head of an alopecic patient in a non-incisional hair transplant, an image processing unit configured to extract an outline pattern of the image of the follicle and the hair by performing a contour detection process or an edge detection process on the image of the follicle and the hair acquired by the image acquiring unit, a follicle shape database configured to store hair pixel patterns related to various shapes of hairs and follicle pixel patterns related to various shapes of follicles, and a follicle determining unit configured to determine whether a follicle is a normal follicle or a defective follicle by comparing the outline pattern of the image of the follicle and the hair with the hair pixel patterns and follicle pixel patterns stored in the follicle shape database.

Further, according to some embodiments of the present invention, an apparatus for automatically separating hair follicles includes a follicle separating unit including a defective hair follicle determining device and configured to cut a skin tissue of a scalp cut from a back of a head of an alopecic patient in units of follicles and to classify follicles by a number of hairs included in each follicle in an incisional hair transplant or to classify follicles each directly extracted from the back of the head of the alopecic patient by the number of hairs included in each follicle in a non-incisional hair transplant and a follicle separation control unit configured to control an operation of the follicle separating unit. The defective hair follicle determining device includes an image acquiring unit configured to acquire an image of a follicle and a hair included in the follicle for each follicle separated from a scalp cut from back of a head of an alopecic patient in an incisional hair transplant or each follicle directly extracted from back of a head of an alopecic patient in a non-incisional hair transplant, an image processing unit configured to extract an outline pattern of the image of the follicle and the hair by performing a contour detection process or an edge detection process on the image of the follicle and the hair acquired by the image acquiring unit, a follicle shape database configured to store hair pixel patterns related to various shapes of hairs and follicle pixel patterns related to various shapes of follicles, and a follicle determining unit configured to determine whether a follicle is a normal follicle or a defective follicle by comparing the outline pattern of the image of the follicle and the hair with the hair pixel patterns and follicle pixel patterns stored in the follicle shape database.

The above and other objects, features, advantages and technical and industrial significance of this invention will be better understood by reading the following detailed descrip-

BEST MODE(S) FOR CARRYING OUT THE INVENTION

Exemplary embodiments of the present disclosure are described in detail below with reference to the accompanying drawings.

In this specification, a skin tissue refers to a tissue cut out from a certain part of a back of a head of an alopecic patient where there are no hair loss genes.

In this specification, a connective tissue refers to a tissue surrounding and supporting units of follicles in the skin tissue.

Figure 1:
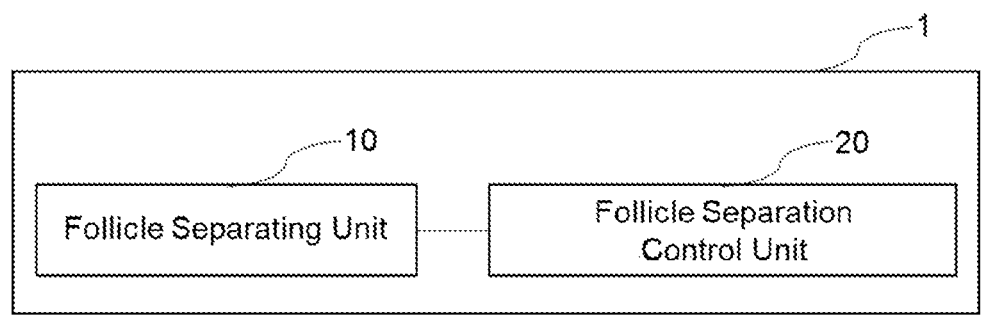
FIG. 1 is a functional block diagram of an automatic hair-follicle separating apparatus according to some embodiments of the present invention.
Figure 2:
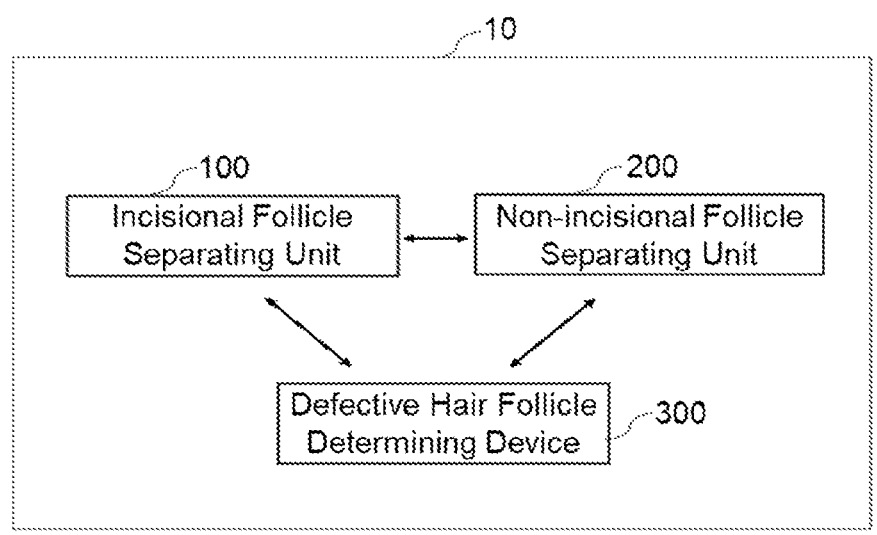
FIG. 2 is a functional block diagram of a follicle separating unit according to some embodiments of the present invention.

FIG. 1 is a functional block diagram of an automatic hair-follicle separating apparatus 1 according to some embodiments of the present invention. FIG. 2 is a functional block diagram of a follicle separating unit 10 according to some embodiments of the present invention.

As shown in FIG. 1, the automatic hair-follicle separating apparatus 1 includes a follicle separating unit 10 and a follicle separation control unit 20.

The follicle separating unit 10 collects various information and data on an image obtained by scanning the scalp cut from a back of a head of an alopecic patient, and after separating units of follicles from a connective tissue without damaging the same, follicles are selected and stored based on the number of hairs formed in each of the separated units of follicles.

As shown in FIG. 2, the follicle separating unit 10 includes an incisional follicle separating unit 100, a non-incisional follicle separating unit 200, and a defective hair follicle determining device (an apparatus for determining defective hair follicles) 300.

The incisional follicle separating unit 100 is configured to scan the scalp cut from the back of the head of the alopecic patient to separate each unit of follicles from the connective tissue formed in the skin tissue, and to select follicles based on the number of hairs included in a unit of follicles.

The non-incisional follicle separating unit 200 cuts and separates the connective tissue attached to the lateral part of the units of follicles, which is extracted directly from the back of the head of an alopecic patient, in units of follicles, and according to the number of hairs included in the units of follicles, the selecting is performed individually.

The defective hair follicle determining device 300 is used, for example, to determine whether a follicle is a normal follicle or a defective follicle from among the follicles selected in the final process of the incisional follicle separating unit 100 or the non-incisional follicle separating unit 200.

Figure 3:
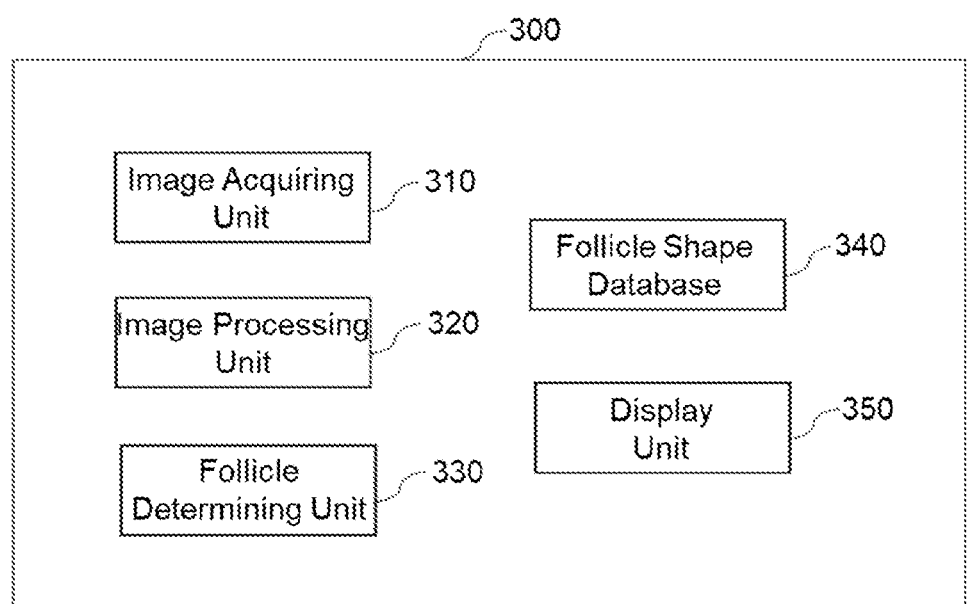
FIG. 3 is a functional block diagram of a defective hair follicle determining device (an apparatus for determining defective hair follicles) according to some embodiments of the present invention.
Figure 4:
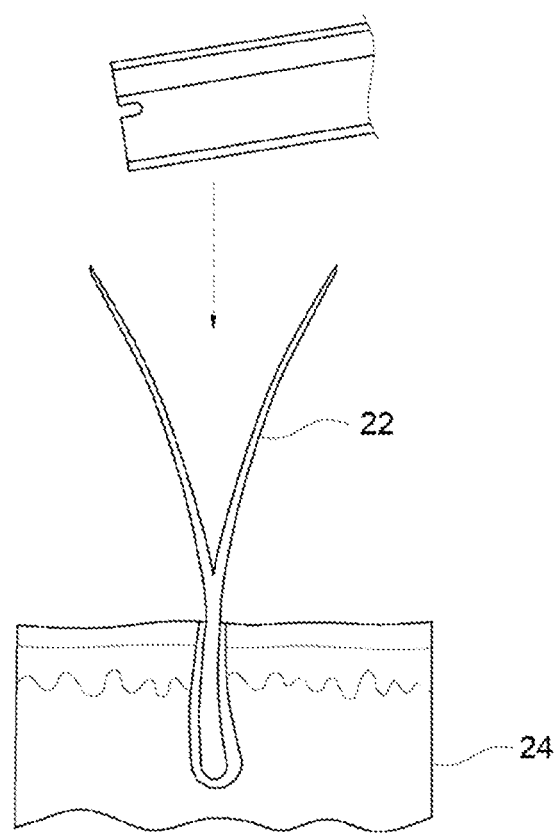
FIG. 4 is a schematic diagram showing a work of cutting a follicle with a blade by a worker.
Figure 5:
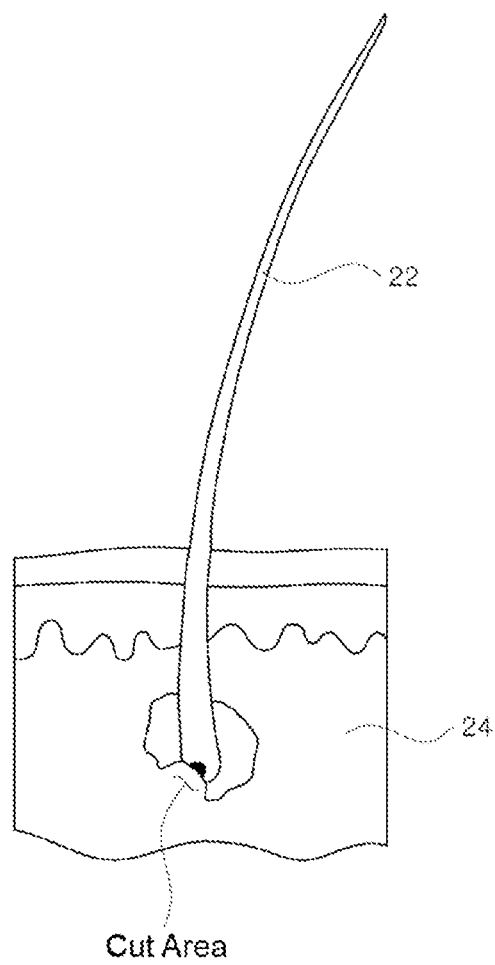
FIG. 5 is a schematic diagram showing a defective hair follicle of which a portion is cut.
Figure 6:
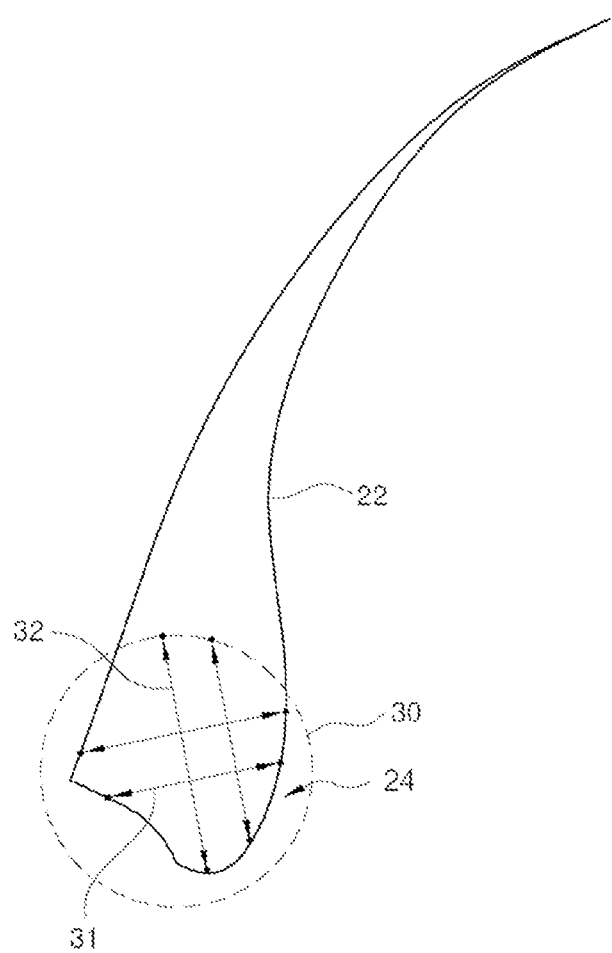
FIG. 6 is a schematic diagram showing a detection of a cut area of a hair follicle according to some embodiments of the present invention.
Figure 7:
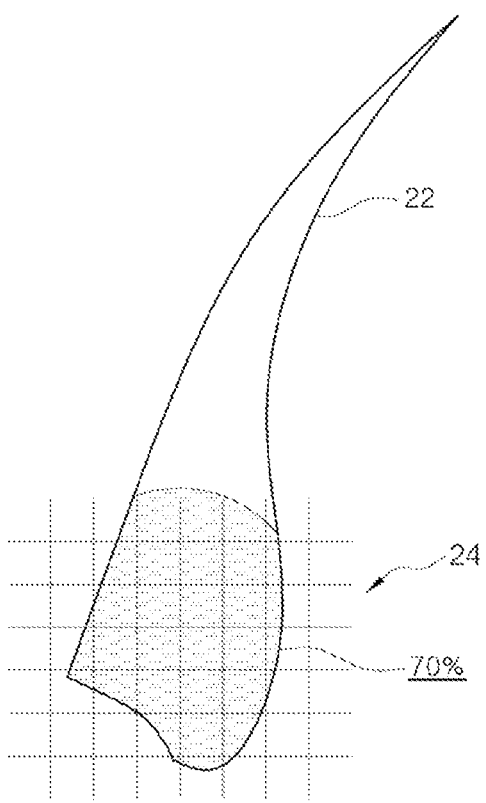
FIG. 7 is a schematic diagram showing an area of a follicle in percentage according to some embodiments of the present invention.

FIG. 3 is a functional block diagram of a defective hair follicle determining device (an apparatus for determining defective hair follicles) 300 according to some embodiments of the present invention. FIG. 4 is a schematic diagram showing a work of cutting a follicle with a blade by a worker. FIG. 5 is a schematic diagram showing a defective hair follicle of which a portion is cut. FIG. 6 is a schematic diagram showing a detection of a cut area of a hair follicle according to some embodiments of the present invention. FIG. 7 is a schematic diagram showing an area of a follicle in percentage according to some embodiments of the present invention.

As shown in FIG. 3, the defective hair follicle determining device 300 includes an image acquiring unit 310, an image processing unit 320, a follicle determining unit 330, a follicle shape database 340, and a display unit 350.

In some embodiments of the present invention, the image acquiring unit 310 uses a laser photosensor to place a follicle at a focal plane and records an image of the follicle with light passing through or reflected from the follicle.

In some embodiments of the present invention, the image acquiring unit 310 records a hair 22 to a follicle 24 with a photosensor array to acquire an image of the hair 22 and the follicle 24.

In some embodiments of the present invention, the image acquiring unit 310 uses laser light as a light source, aligns a focal point of the hair 22 with a focal point of a sensing pinhole with the light from the point source, and measures a hair region with a portion other than the focal plane not showing in the image. The image acquiring unit 310 can use a confocal laser scanning microscope.

Although it is described that the image acquiring unit 310 uses a laser light source in the above example, the present invention is not limited to this scheme, but various recording means can be used such as an ultrasonic sensor array, an infrared sensor array, and the like.

The image acquiring unit 310 can measure a minute change of reflected light from a single hair using the confocal laser scanning microscope or visualize the internal structure by scanning the area from the hair 22 to the follicle 24. A two-dimensional image can be reconstructed as a three-dimensional image with the help of a computer software program.

In some embodiments of the present invention, the image acquiring unit 310 includes a light emitting unit for emitting light of a predetermined wavelength towards a follicle and a light receiving unit for receiving reflected light from the follicle and converts the received light into an electrical signal.

In some embodiments of the present invention, the light emitting unit includes a light-emitting element array having a plurality of light-emitting elements arranged in an arrayed manner and a light-receiving element array having a plurality of light-receiving elements respectively corresponding to the plurality of light-emitting elements.

In some embodiments of the present invention, the image processing unit 320 converts the acquired image of the hair 22 and the follicle 24 into a grayscale image, removes a noise signal from the grayscale image, passes the noise-free image through a sharpening filter, and emphasizes edges of the image.

After emphasizing the edges of the image, the image processing unit 320 performs a contour detection process or an edge detection process to extract the edge of the image.

The image processing unit 320 processes the image of the hair 22 and the follicle 24 as black (pixel value 0) and the background other than the image of the hair 22 and the follicle 24 as while (pixel value 255).

The follicle shape database 340 stores hair pixel patterns related to various shapes of hairs and follicle pixel patterns related to various shapes of follicles.

The follicle determining unit 330 compares an edge pattern of the extracted image of the hair 22 and the follicle 24 with the hair pixel patterns and the follicle pixel patterns stored in the follicle shape database 340 and classifies a final image of the hair 22 and the follicle 24.

The follicle determining unit 330 sets the edge forming the final image of the follicle 24 as an interest area 30, and then builds pixel coordinates by spatially divides the interest area 30.

The follicle determining unit 330 extracts an edge area in the interest area 30, and then counts the number of pixels for each line in the edge area.

Typically, a single follicle has a predetermined width, and the follicle shape database 340 stores shapes of reference follicles corresponding to the width of the follicle. The shape of the reference follicle includes an outline of a follicle and the number of reference pixels forming the shape of the follicle.

The follicle determining unit 330 draws a plurality of horizontal imaginary lines 31 in the horizontal direction and a plurality of vertical imaginary lines 32 in the vertical direction on black pixels at a plurality of positions in the edge area (see FIG. 6).

The follicle determining unit 330 calculates a distance between black pixels based on pixel coordinates on each horizontal imaginary line and pixel coordinates on each vertical imaginary line and sets the maximum distance among the distances between black pixels as a width of the edge area representing a follicle area.

The follicle determining unit 330 searches a shape of a follicle and the number of reference pixels corresponding to the edge area referring to the follicle shape database 340.

The follicle determining unit 330 calculates the rate of the number of counted pixels to the number of searched reference pixels to measure the percentage of the follicle area.

For example, when the number of searched reference pixels is 100) and the number of counted pixels is 70, the percentage of the follicle area is 70%.

The follicle determining unit 330 determines whether the percentage of the follicle area is equal to or more than a predetermined percentage of a normal follicle (70%) or not, if the percentage of the final follicle area is equal to or more than the percentage of the normal follicle, determines that the follicle is a normal follicle, and if the percentage of the final follicle area is less than the percentage of the normal follicle, determines that the follicle is a defective follicle.

In some embodiments of the present invention, the follicle determining unit 330 changes the predetermined percentage of the normal follicle, and then determines whether the follicle is a normal follicle or a defective follicle based on the changed percentage of the normal follicle.

The follicle determining unit 330 can change the predetermined percentage of the normal follicle to 60%, 80%, and the like. The follicle 24 has different survival rate depending on how much percentage the normal follicle occupies in the entire follicle.

In some embodiments of the present invention, the follicle determining unit 330 magnifies the edge area with a predetermined zoom ratio, and then outputs the magnified image with the percentage calculated in the follicle area and the percentage of the cut area to the display unit (see FIG. 7).

In some embodiments of the present invention, the follicle shape database 340 stores an outline of a reference follicle related to the shape of the follicle, a pixel pattern of the reference follicle, and the number of reference pixels.

The follicle determining unit 330 compares the pixel pattern forming the extracted outline with the pixel pattern of the reference follicle stored in the follicle shape database 340 to count the number of pixels for each line in the edge area, calculates the percentage of the number of counted pixels to the number of reference pixels, determines whether the calculated percentage is equal to or more than the predetermined percentage of the normal follicle or not, if the calculated percentage is equal to or more than the predetermined percentage of the normal follicle, determines that the follicle is a normal follicle, and if the calculated percentage is less than the predetermined percentage of the normal follicle, determines that the follicle is a defective follicle.

As described above, the follicle determining unit 330 determines whether a follicle is a normal follicle or a defective follicle based on the pixel pattern forming the outline pattern and the pixel pattern of the reference follicle stored in the follicle shape database 340. However, the present invention is not limited to this scheme, but the pixel-related operation can be substituted with a physical magnitude-related operation.

For example, a magnitude-based method can be used based on a hardware-fixed value (e.g., FOV setting and resolution of a camera, distance between a camera and an object) and a depth camera (stereographic scheme using a plurality of cameras, Lidar, ToF camera, or the like).

In the process of substituting the pixel-related operation with the physical magnitude-related operation, it is possible to determine whether a follicle is a normal follicle or a defective follicle via a process similar to the process of using the pixel by calculating a physical distance scale per pixel and converting pixel information into distance information using the scale.

Figure 8:
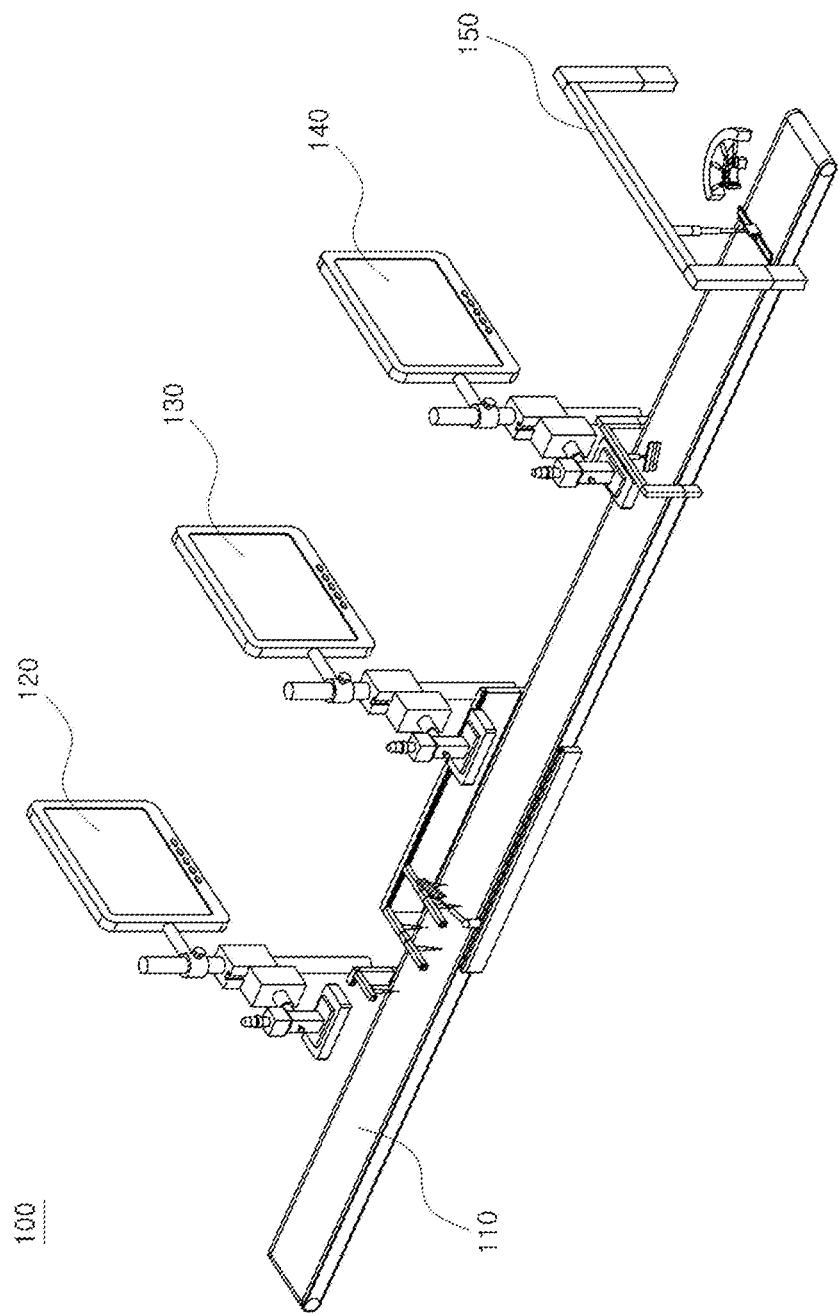
FIG. 8 is a perspective view of the automatic hair-follicle separating apparatus according to some embodiments of the present invention.

As shown in FIG. 8, the incisional follicle separating unit 100 includes a conveyor belt unit 110, a scalp data analyzing unit 120, a first cutting unit 130, a second cutting unit 140 and a follicle selective unit 150.

The conveyor belt 110 is a conveyor belt formed horizontally from a leading end to a trailing end and configured to rotate in a single linear direction by a rotation of a driving motor controlled by the follicle separation control unit 20 to transport the connective tissue including a unit of follicles positioned on one side above the conveyor belt 110.

The conveyor belt 110 is configured to have a locking projection formed protruding to the left and right peripheral ends of a belt rail such that an antibacterial cutting plate 111 (see FIG. 19) is fitted and coupled along the central periphery.

The antibacterial cutting plate 111 directly supports the skin tissue including the follicles and transports the skin tissue according to the rotation of the conveyor belt 110.

Figure 19:
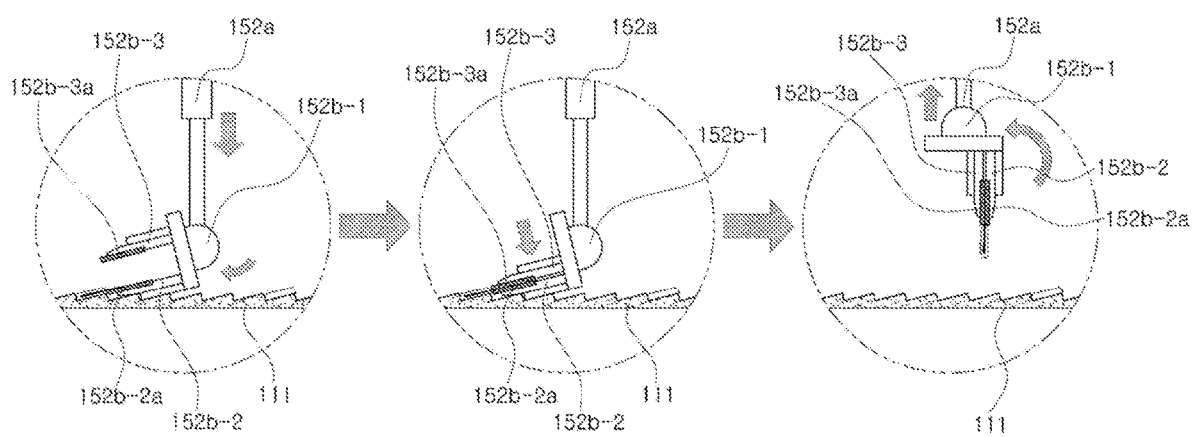
FIG. 19 is a schematic diagram showing an operation procedure of a selective follicle transporting unit according to some embodiments of the present invention.

As shown in FIG. 19, the antibacterial cutting plate 111 is sterilized by a belt having a repetitive sawtooth shape pattern with a slope heading upward in a forward direction and formed of an antibacterial, corrosion-resistant and elastic material (for example, silicon).

The antibacterial cutting plate 111 prevents contamination and damage of follicles by blocking infection caused by exposure to bacteria through the side of the connective tissue in direct contact cut from a patient.

According to some embodiments of the present invention, the antibacterial cutting plate 111 is composed of disposable consumables that are discarded when follicle separation is completed in consideration of hygiene issues.

The scalp data analyzing unit 120 scans the cut skin tissue to measure the average density of hairs formed in the scalp, measures the hardness of the skin tissue, and collects datafi-cated information.

Figure 9:
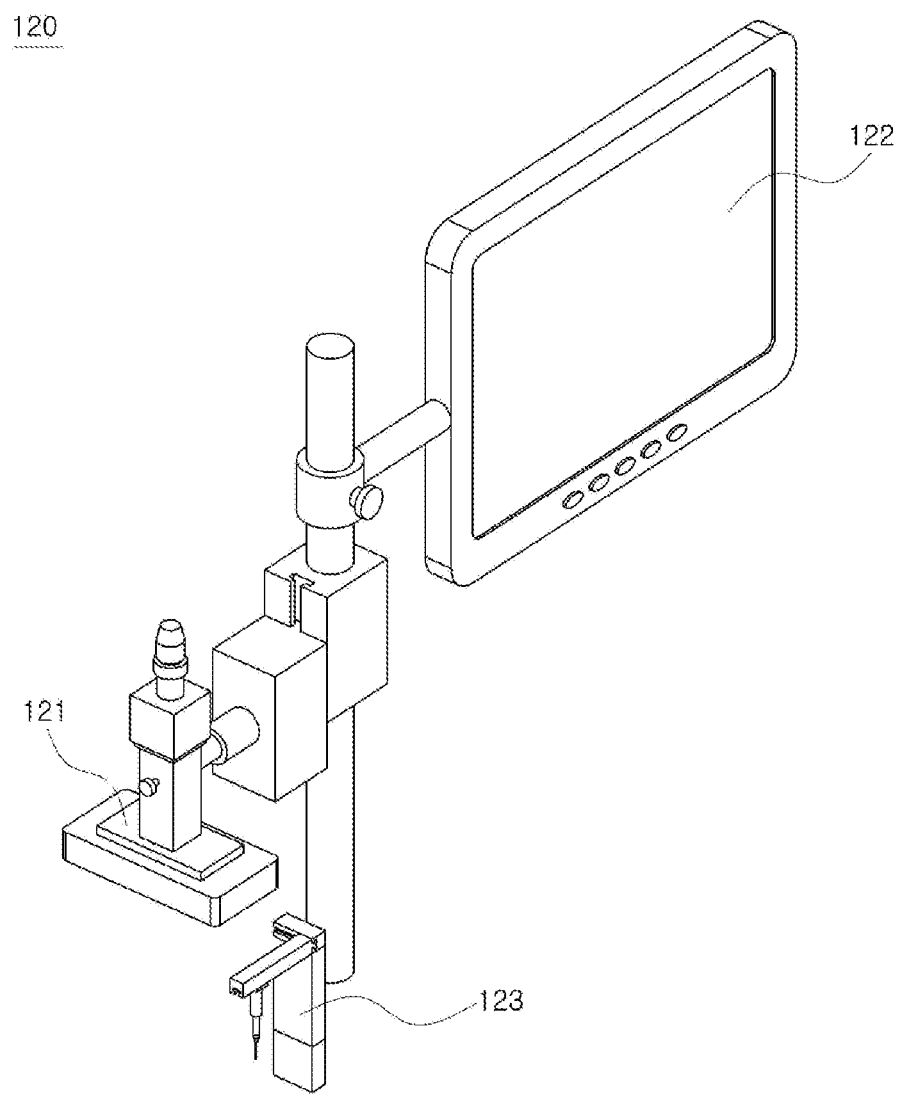
FIG. 9 is a perspective view of a scalp data analyzing unit according to some embodiments of the present invention.

As shown in FIG. 9, the scalp data analyzing unit 120 includes a scanning unit 121, a monitor unit 122, and a skin hardness measuring unit 123.

The scanning unit 121 is positioned in the vertical direction on an upper side of a conveyor belt unit, and is configured to include moving up and down along a scanning guide rail formed in an up-and-down direction, scanning a cut skin tissue as a whole to determine a follicle distribution, and measuring an interval between follicles to determine an average density of the hair in the skin tissue.

According to some embodiments of the present invention, the scanning unit 121 scans the whole skin tissue by moving up and down in an up-and-down direction according to the size and length of the cut skin tissue and adjusting the focal length, and it is possible to zoom in/out of the portion to be scanned to provide the monitor unit 122 with a partially enlarged and reduced screen.

The monitor unit 122 enlarges and displays the screen scanned by the scanning unit 121, and outputs the information measured by the skin hardness measuring unit 123 to the screen.

That is, the monitor unit 122 allows a doctor to visually check the overall state of the cut skin tissue, and provides information on the skin hardness measured by the skin hardness measuring unit 123.

According to some embodiments of the present invention, the skin hardness measuring unit 123 is positioned to be supported by one side of the left side of the conveyor belt, a skin hardness measuring pin moves in x and y directions in the upper direction of the conveyor belt, and when a skin tissue is detected by a skin tissue sensor for the first time, it is lowered vertically and the skin hardness measuring pin positioned at a lower end measures the intensity of the force piercing through the scalp tissue.

Figure 10:
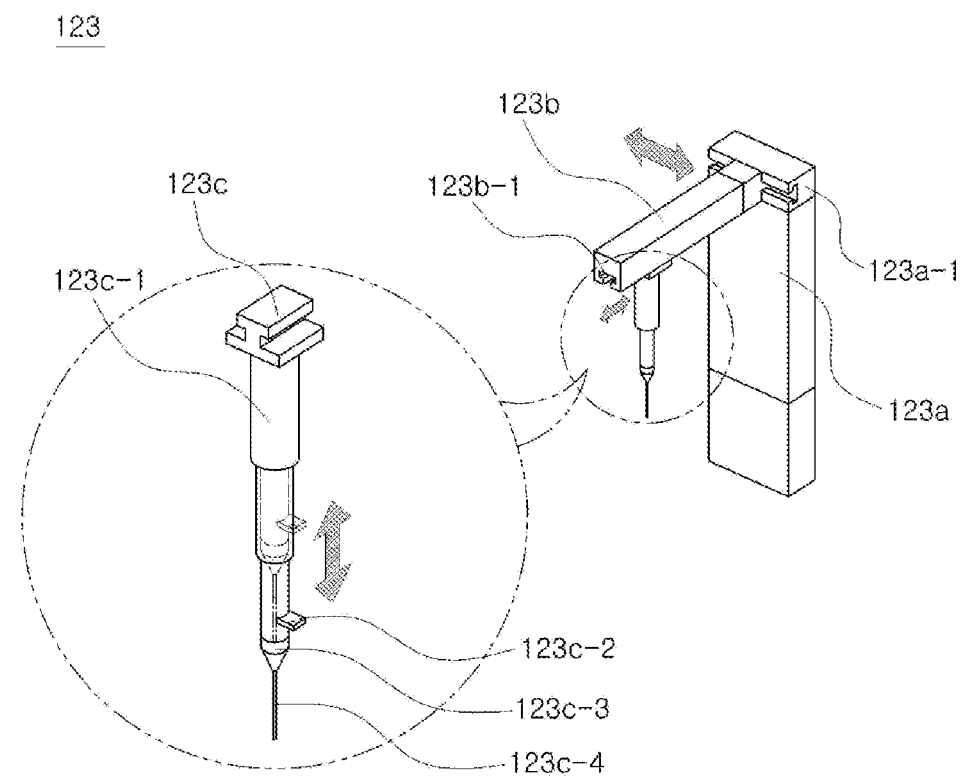
FIG. 10 is a perspective view of a skin hardness measuring unit according to some embodiments of the present invention.

As shown in FIG. 10, the skin hardness measuring unit 123 includes a hardness measuring support 123a, an x-axis moving bar 123b, and a y-axis moving unit 123c.

The hardness measuring support 123a is a rectangular plate shape formed upright on one side of the left side surface of the conveyor belt 110 in the traveling direction of the conveyor. An x-axis guide rail 123a-1 configured to be movable in the x direction, which is the conveyor traveling direction, is formed in the upper inner direction. This allows an x-axis moving bar 123b to reciprocate in the x direction within the range of the x-axis guide rail 123a-1.

The x-axis moving bar 123b is a straight bar formed perpendicular to the conveyor travel direction, is coupled to the x-axis guide rail 123a-1, and moves in the x direction which is the conveyor travel direction, and a y-axis guide rail 123b-1 which is movable in the y direction is formed on the bottom surface. Through this, the y-axis moving unit 123c is reciprocated in the y direction within the range of the y-axis guide rail 123b-1.

The y-axis moving unit 123c is inserted into the y-axis guide rail 123b-1 to form a hydraulic cylinder 123c-1 that moves in the y direction and moves up and down in the vertical lower direction, and a skin tissue sensor 123c-2 is formed on one side of a lower end of the hydraulic cylinder 123c-1, and a skin hardness measuring pin 123c-3 is formed on the lower end of the hydraulic cylinder 123c-1.

When the skin tissue sensor 123c-2 is located in front of the conveyor belt unit and when a skin tissue moving backwards is detected for the first time, the skin tissue sensor 123c-2 transmits the detection information to the follicle separation control unit 20 to stop the rotation of the conveyor belt 110. In addition, the hydraulic cylinder 123c-1 is moved down to measure the intensity of force of the skin hardness measurement pin 123c-3 piercing through the skin tissue to provide to the follicle separation control unit 20.

At this time, a pressure sensor is formed inside the skin hardness measurement pin 123c-3 to measure the pressure applied when the lower pin penetrates the skin tissue. The cutting force of the first cutting blade follicle separation control unit 134 and the second cutting blade follicle separation control unit 143 are set depending on the measured intensity of the pressure.

The lower pin 123c-4 is detachably coupled to the lower end of the skin hardness measuring pin 123c-3 to facilitate replacement and repair.

The first cutting unit 130 is positioned at a rear end of the scalp data analyzing unit 120 in the traveling direction of the conveyor belt to set the moving interval of the cutting blades according to the measured density from the scalp data, and cuts the scalp tissue into thin slices.

Figure 11:
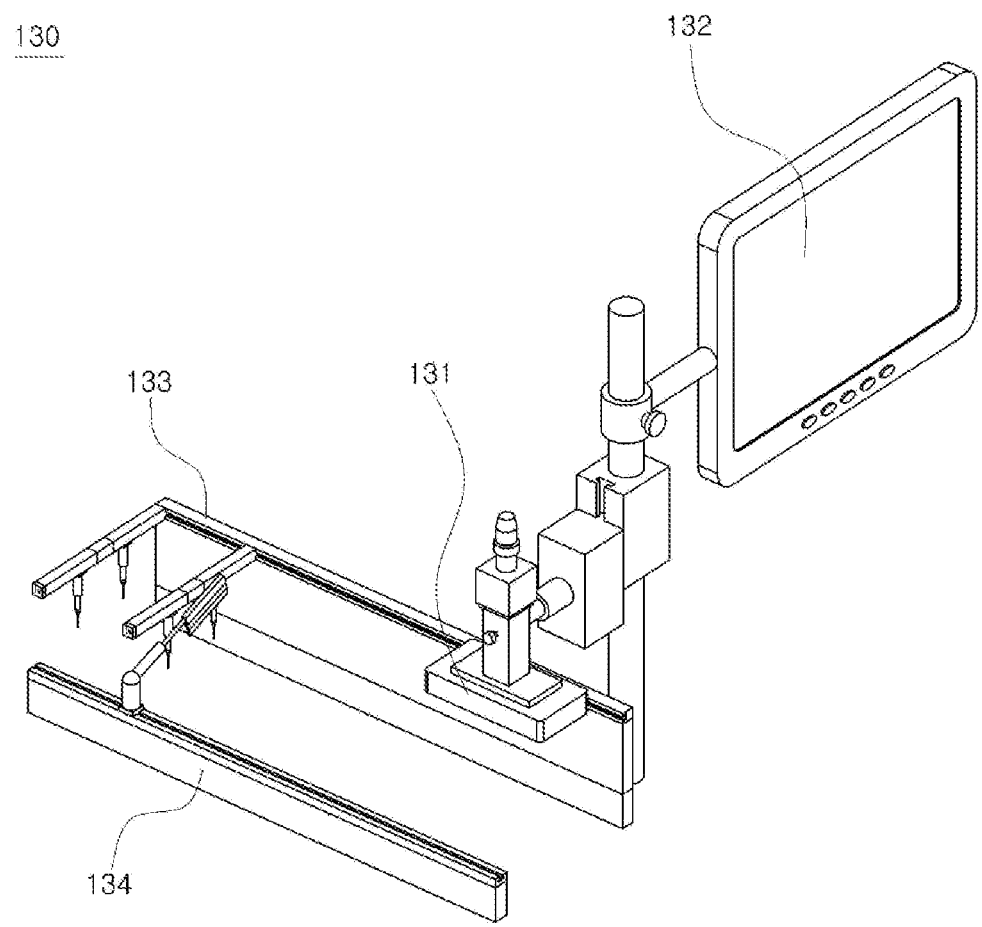
FIG. 11 is a perspective view of a first cutting unit according to some embodiments of the present invention.

As shown in FIG. 11, the first cutting unit 130 includes a first cutting scanning unit 131, a first monitor 132, a first pin fixing unit 133, and a first cutting blade follicle separation control unit 134.

The first cutting scanning unit 131 having a rectangular shape is positioned in a vertical direction on one side of an upper end of the conveyor belt, and moves up and down along the scanning guide rail formed in the vertical direction, scanning the front of the cut skin tissue to check the cutting position and recording an image of slicing the skin tissue in real time.

The first cutting scanning unit 131 scans the whole skin tissue by adjusting the focal length by moving up and down in the vertical direction according to the variable cutting position, and it is possible to zoom in/out of a portion to be scanned to provide a partially enlarged and reduced screen to the first monitor unit 132.

The first monitor unit 132 enlarges and displays the screen scanned by the first cutting scanning unit 131, so that a doctor can visually check the state of the front of the skin tissue and the screen information of being cut into slices.

The pin fixing unit 133 is supported on one side of the left side of the conveyor belt, and detects the position of the skin tissue identified by the scan in the first cutting scanning part, so that the vertical support pins located on the left and right sides of the front and rear are moved to the x and y directions. When the skin tissue is detected by the skin tissue sensor coupled to each vertical support pin which is moved in the axial direction, the pin fixing unit 133 moves down in the vertical direction to fix the skin tissue.

Figure 12:
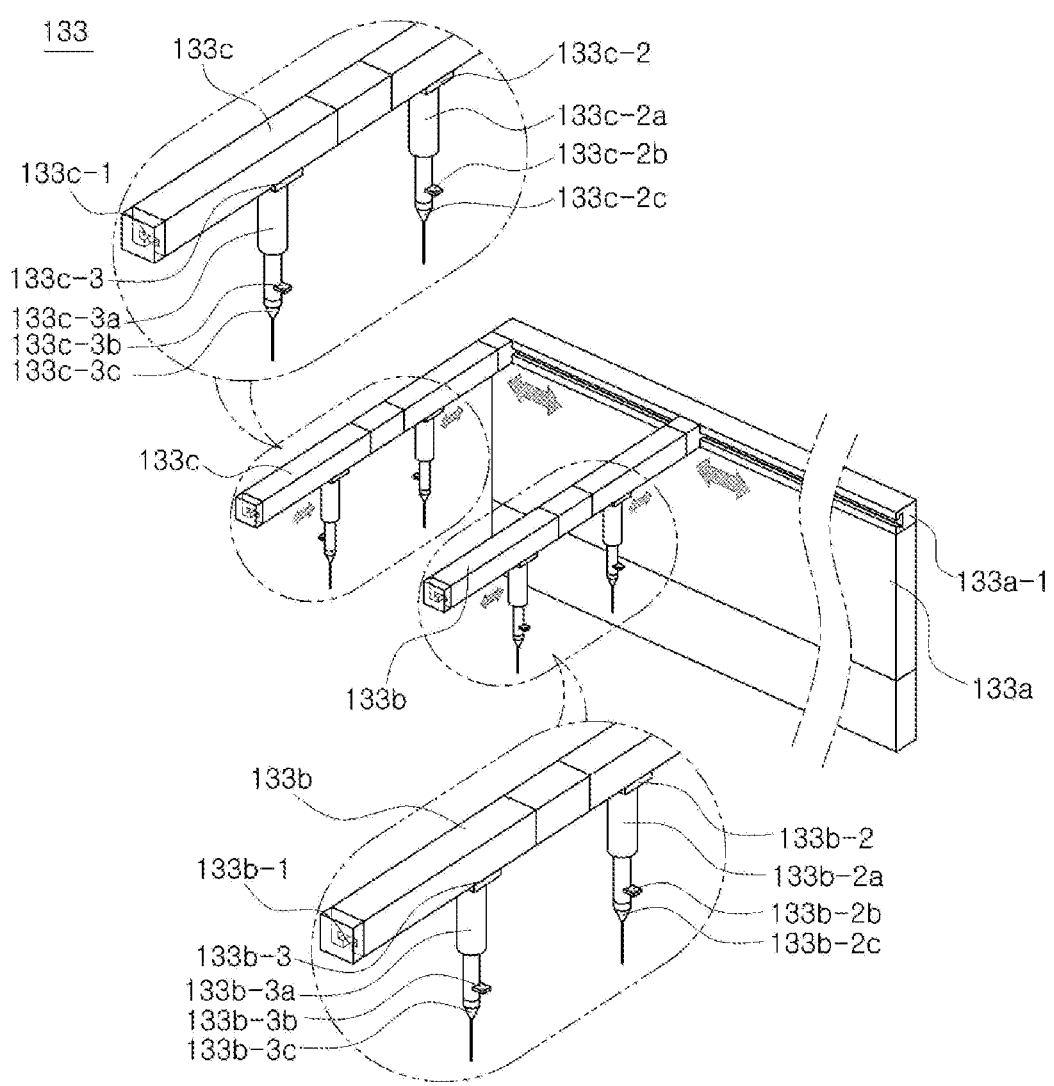
FIG. 12 is a perspective view of a pin fixing unit according to some embodiments of the present invention.

As shown in FIG. 12, the pin fixing unit 133 includes a pin fixing support 133a, a front pin fixing bar 133b, and a rear pin fixing bar 133c.

The pin fixing support 133a has a rectangular plate shape formed upright on one side of the left side surface of the conveyor belt 110 in the traveling direction of the conveyor. An x-axis guide rail 133a-1 movable in the x direction which is the traveling direction of the conveyor is formed in the upper inside direction. This allows the front pin fixing bar 133b and the rear pin fixing bar 133c to reciprocate in the x direction within the range of the x-axis guide rail 133a-1.

The front pin fixing bar 133b has a straight bar shape formed perpendicular to the conveyor traveling direction, is coupled to the x-axis guide rail 133a-1, and is moved in the x direction which is the conveyor traveling direction, and a y-axis guide rail 133b-1 is formed longitudinally at the bottom surface, and a front left pin support 133b-2 and a front right pin support 133b-3 are coupled to the y-axis guide rail.

The front left pin support 133b-2 has a hydraulic cylinder 133b-2a whose upper end is inserted into the y-axis guide rail 133b-1 and is moved in the y direction and moves up and down in the vertical lower direction. The skin tissue sensor 133b-2b is formed at one lower end of the hydraulic cylinder 133b-2a, and the front left pin 133b-2c is formed at the lower end of the hydraulic cylinder 133b-2a.

The front right pin support part 133b-3 has a hydraulic cylinder 133b-3a whose upper end is inserted into the y-axis guide rail 133b-1 and is moved in the y direction and moves up and down in the vertical lower direction. The skin tissue sensor 133b-3b is formed at one lower end of the hydraulic cylinder 133b-3a, and the front right pin 133b-3c is formed at the lower end of the hydraulic cylinder 133b-3a.

The rear pin fixing bar 133c is coupled to the x-axis guide rail 133a-1 in the shape of a straight bar formed perpendicularly to the conveyor traveling direction and moved in the x direction which is the conveyor traveling direction, and a y-axis guide rail 133c-1 is formed longitudinally at the bottom surface, and the rear left pin support 133c-2 and the rear right pin support 133c-3 are coupled to the y-axis guide rail.

The rear left pin support part 133c-2 has a hydraulic cylinder 133c-2a whose upper end is inserted into the y-axis guide rail 133c-1 and is moved in the y direction and moves up and down in the vertical lower direction. The skin tissue sensor 133c-2b is formed at one lower end of the cylinder 133c-2a, and a rear left pin 133c-2c is formed at the lower end of the hydraulic cylinder 133c-2a.

The rear right pin support part 133c-3 has a hydraulic cylinder 133c-3a whose upper end is inserted into the y-axis guide rail 133c-1 and is moved in the y direction and moves up and down in the vertical lower direction. The skin tissue sensor 133c-3b is formed at one lower end of the cylinder 133c-3a, and a rear right pin 133c-3c is formed at the lower end of the hydraulic cylinder 133c-3a.

According to some embodiments of the present invention, the front left pin 133b-2c and the front right pin 133b-3c are spaced apart from the rear of the first cutting blade follicle separation control unit 140 so that the front left and right sides of the skin tissue are pierced and supported in the vertical direction. The rear left pin 133c-2c and the rear right pin 133c-3c support and pierce the rear left and right sides of the skin tissue in the vertical direction, so that when the front side of the skin tissue is cut in a sliced form through the first cutting blade 134d-1, the skin tissue is prevented from being pushed and moved to another position, supporting stable cutting to be performed.

Also, according to some embodiments of the present invention, the front left pin 133b-2c is detachably screw-coupled to the lower end of the hydraulic cylinder 133b-2a, the front right pin 133b-3c to the lower end of the hydraulic cylinder 133b-2a, the rear left pin 133c-2c to the lower end of the hydraulic cylinder 133c-2a, and the rear right pin 133c-3c to the lower end of the hydraulic cylinder 133c-a, respectively, thereby facilitating replacement and repair.

This is to facilitate replacement when the pin is damaged during the cutting operation, and to replace the follicles after the separation of the follicles from the patient's connective tissue, thereby maintaining a clean sanitary condition at the time of follicle separation of the next patient.

The first cutting blade follicle separation control unit 134 is supported and positioned on one side of the right side of the conveyor belt, and a hydraulic cylinder having a blade fixed to the front perpendicularly to the conveyor belt travel direction is formed, rotates at a constant speed in the vertical direction, and descends. The skin tissue is cut into slices while reciprocating back and forth by a hydraulic cylinder.

Figure 13:
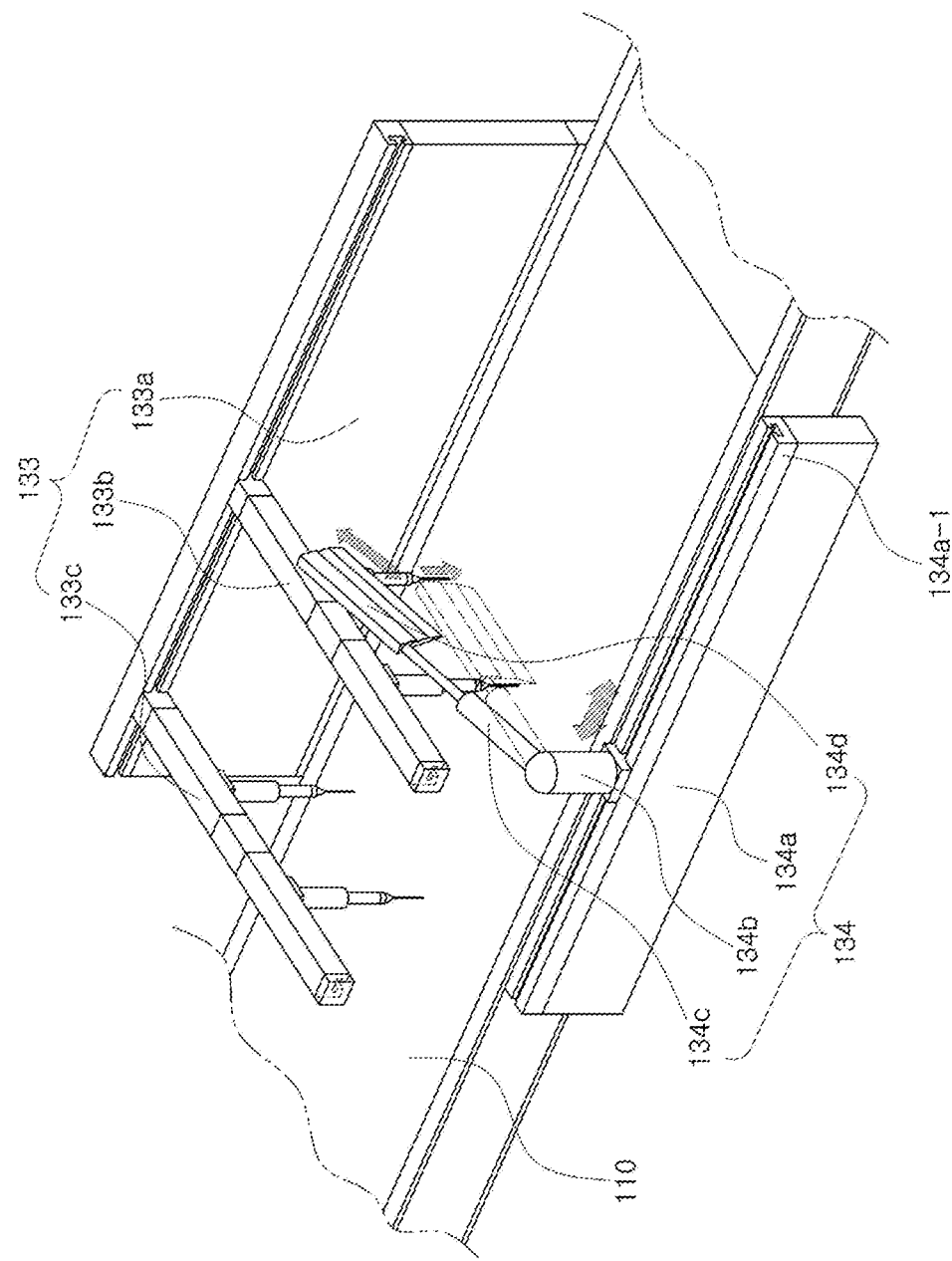
FIG. 13 is a perspective view of a first cutting unit according to some embodiments of the present invention.

As shown in FIG. 13, the first cutting blade follicle separation control unit 134 includes a first cutting blade support 134a, a first cutting rotary unit 134b, a first cutting hydraulic cylinder 134c, and a first cutting blade frame 134d.

The first cutting blade support 134a is a rectangular plate shape formed upright on one side of the right side surface of the conveyor belt 110 in the traveling direction of the conveyor. An x-axis guide rail 134a-1 movable in the x direction which is the traveling direction of the conveyor is formed in the upper inner direction. This allows the first cutting rotary unit 134b to reciprocate in the x direction within the range of the x-axis guide rail 134a-1.

The first cutting rotary unit 134b supports the first cutting hydraulic cylinder 134c perpendicularly to the conveyor traveling direction and moves in the x direction, and a rotating shaft is formed based on one side of the upper center to rotate the first cutting hydraulic cylinder 134c in an up-and-down direction.

Figure 14:
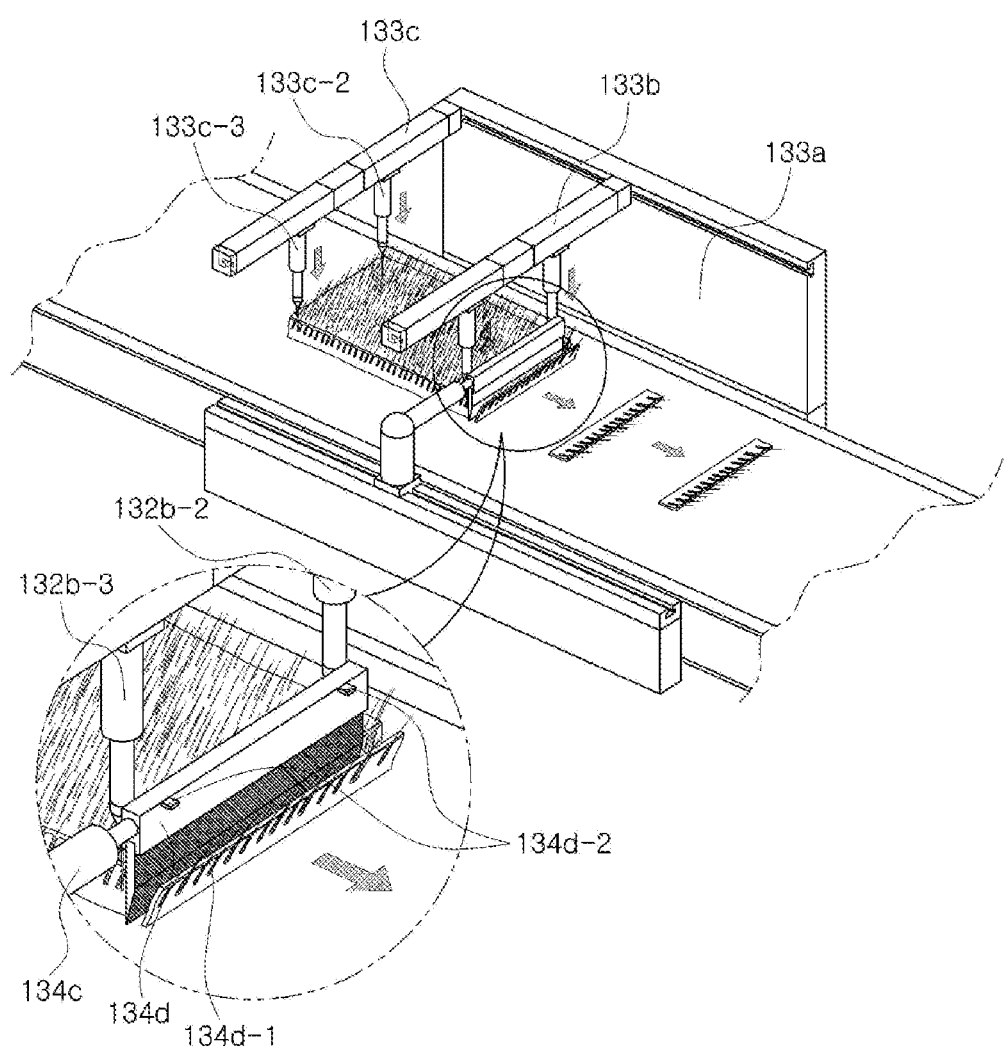
FIG. 14 is a perspective view of a pin fixing unit according to some embodiments of the present invention with a related enlarged diagram.

When the first cutting blade 134d-1 (see FIG. 14) cuts the skin tissue, the first cutting rotation part 134b slowly moves down within an angle range of 30° to −2°, and when the skin tissue is cut into slices, it moves up rapidly to prepare for the next process.

In a state where the first cutting blade 134d-1 is maintained at an angle of about 30° based on the first cutting rotary unit, when the skin tissue including a unit of follicles is located in the lower direction, the first cutting blade 134d-1 moves downward in the left and right directions, down to an angle of −2° to cut the skin tissue including the units of follicles in a slice form up to an upper side of the antibacterial cutting plate 111. This allows the skin tissue, including the units of follicles, to be completely cut into slices.

The first cutting hydraulic cylinder 134c is axially coupled perpendicularly to the upper inward direction of the first cutting rotary unit 134b and the first cutting blade frame 134d is coupled to the end of the cylinder to reciprocate the first cutting blade frame 134b through the reciprocation movement of the cylinder.

The first cutting hydraulic cylinder 134c reciprocates the first cutting blade frame 134d to stably cut the elastic skin tissue in a slice form.

The first cutting blade frame 134d is coupled to the end of the first cutting hydraulic cylinder 134c, and the first cutting blade 134d-1, which is easily coupled and detachably fitted in the lower direction, and a skin tissue sensor 134d-2 is formed at the front left and right sides.

Upon detection of the front part of the skin tissue positioned in a lower direction through skin tissue sensor 134d-2 formed at the front left and right sides, the first cutting blade frame 134d is lowered gradually in the vertical direction by the first cutting rotary unit 134b and reciprocated by the first cutting hydraulic cylinder 134c to cut the skin tissue into slices.

The second cutting unit 140 is formed upright in the rear end direction of the first cutting unit 130 to the left of the conveyor belt travel direction, the cutting blade is reciprocated in the vertical direction of the conveyor belt, and the each unit of follicles are individually separated by scanning each unit of follicles of the skin tissue cut into slices and cutting the left and right side portions respectively in the first cutting device.

According to some embodiments of the invention, the second cutting unit 140 further removes the tissue attached to the side portion of each incision of the units of follicles.

According to some embodiments of the present invention, the automatic hair-follicle separating apparatus 1 may further include a third cutting device unit (not shown) for removing tissue attached to the side portion of each unit of follicles cut between the second cutting unit 140 and the follicle selective unit 150.

Figure 15:
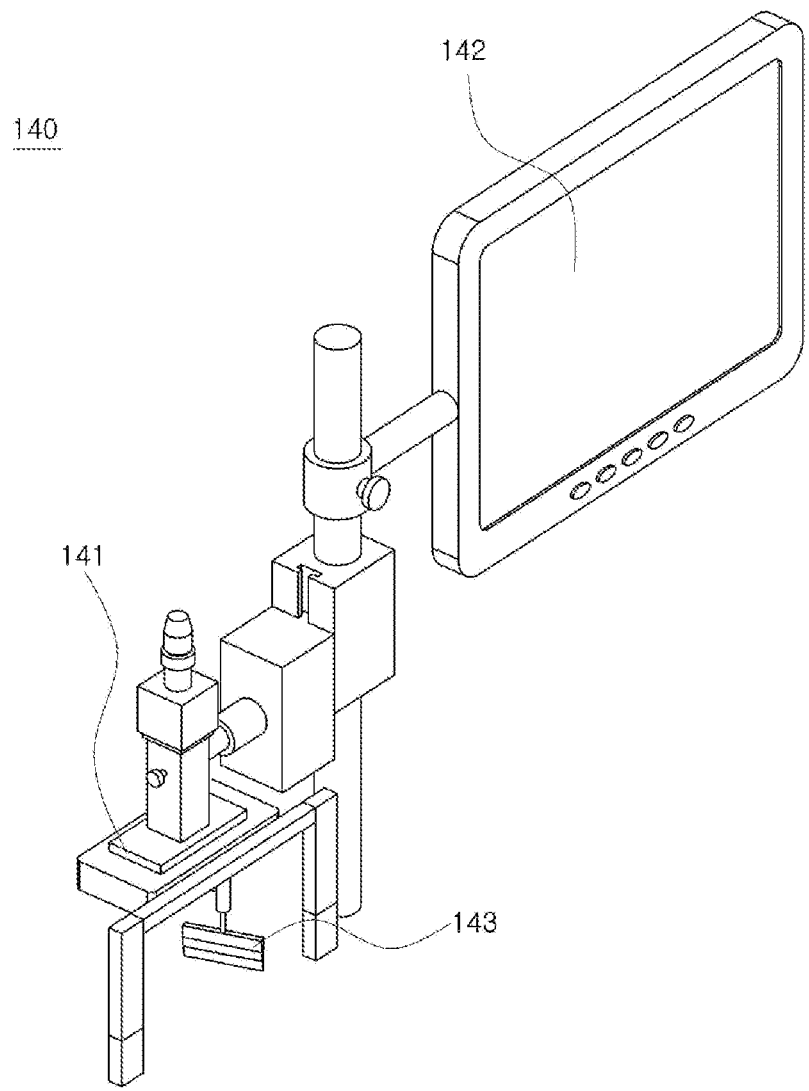
FIG. 15 is a perspective view of a second cutting unit according to some embodiments of the present invention.

As shown in FIG. 15, the second cutting unit 140 includes a second cutting scanning unit 141, a second monitor unit 142, and a second cutting blade follicle separation control unit 143.

The second cutting scanning unit 141 has a rectangular shape positioned in the center of one side of the upper end of the conveyor belt, and identifies the unit of follicles by scanning the connective tissue cut into slices by moving up and down along a scanning guide rail formed in a vertical direction. In addition, the position and direction information of the identified units of follicles is provided to the follicle separation control unit, and an image of scalp tissue being cut into slice shaped unit of follicles is taken in real time.

The second cutting scanning unit 141 moves up and down in the vertical direction and adjusts a focal length according to a variable cutting position to scan the connective tissue having a slice shape, and it is possible to zoom in/out of a portion to be scanned to provide a partially enlarged and reduced screen to the second monitor unit 142.

The second monitor unit 142 is located on the left side of the upright second cutting unit 140, and enlarges and displays the screen scanned by the second cutting scanning unit 141, so that a doctor can visually check the state of the slice shaped connective tissue and the screen information of cutting into units of follicles.

The second cutting blade follicle separation control unit 143 is a "⊏" shaped frame rotated 90 degrees clockwise (⊓) across the top of the conveyor belt, and the cutting blade reciprocates in the lower direction of the frame. The left and right sides of the units of follicles included in the sliced connective tissue are cut at regular intervals and separated into units of follicles individually.

Figure 16:
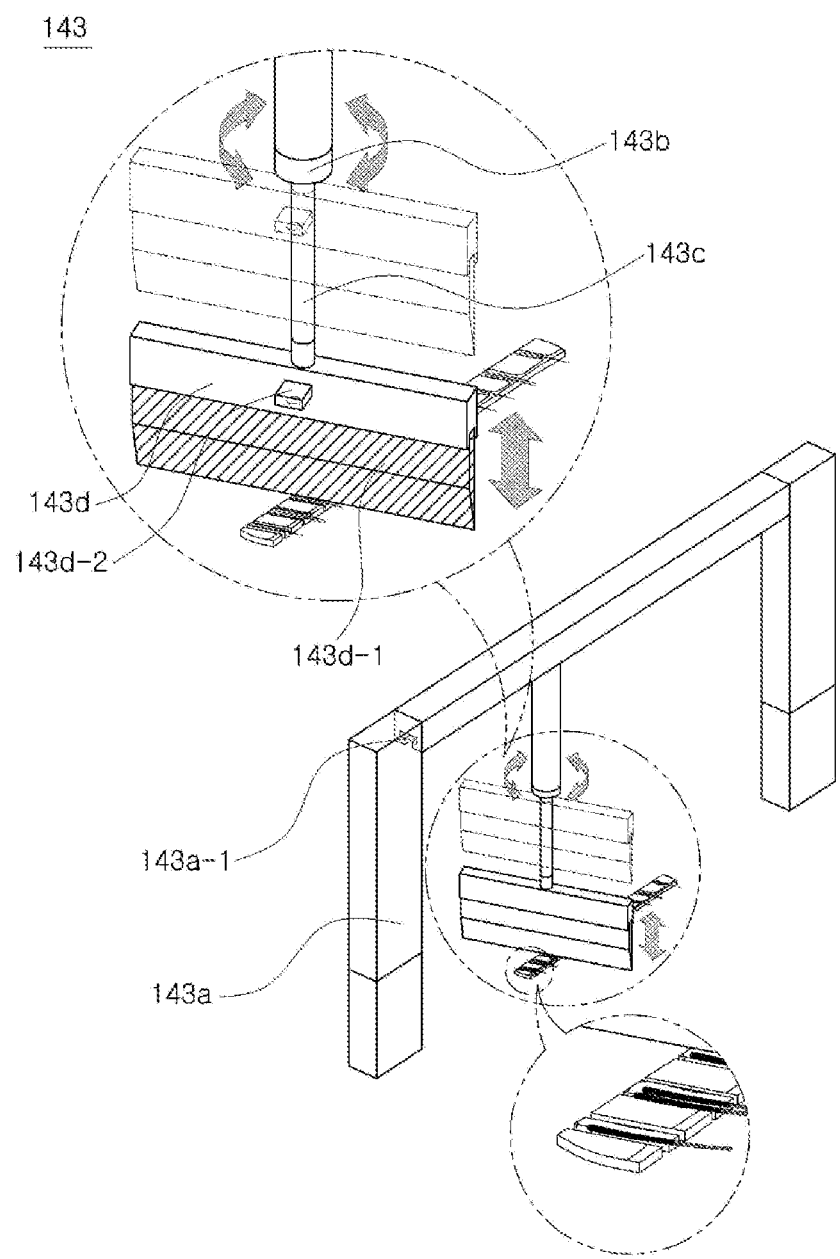
FIG. 16 is a perspective view showing a second cutting blade cutting a sliced connective tissue.

As shown in FIG. 16, the second cutting blade follicle separation control unit 143 includes a cutting blade support 143a, the second cutting rotary unit 143b, the second cutting hydraulic cylinder 143c, and the second cutting blade frame 143d.

The cutting blade support 143a is a "⊏" shaped frame rotated 90 degrees clockwise (⊓) across the top of the conveyor belt in the vertical direction, and a vertical guide rail 143a-1 is formed in the lower direction which reciprocates the second cutting rotary unit 143b in the vertical direction.

The second cutting rotary unit 143b has an upper end coupled to the vertical guide rail 143a-1 of the cutting blade support 143a, and rotates in a horizontal direction to form the second cutting hydraulic cylinder 143c and the second cutting blade frame 143d.

The second cutting rotary unit 143b receives the position and direction information of the follicles primarily through the second cutting scanning unit 141 and secondarily receives the position and direction information of the follicles through the follicle position sensor 143d-2. After receiving the information and moving to a position in the side vertical direction of the follicles, the second cutting rotary unit 143b rotates in the horizontal direction according to the direction of the follicles to set the position and direction for cutting only the left and right sides of the follicle in the slice shaped connective tissue.

Through this, regardless of the condition of the worker, the left and right sides of the slice-shaped connective tissue can be cut and separated without damage according to the direction of the follicles, thereby improving the engraftment rate of the follicles.

The second cutting hydraulic cylinder 143c has a cylinder shape coupled to the lower end of the second cutting rotary unit 143b and moves the second cutting edge frame positioned at the lower end while moving down and up in the vertical direction.

The second cutting blade frame 143d has a rectangular frame shape coupled to the lower end of the second cutting hydraulic cylinder 143c, and the second cutting blade 143d-1 is detachably coupled to the lower end by fitting. The follicle position sensor 143d-2 is configured to detect the position and the direction of the follicle in the lower direction in the center of the front upper side.

According to some embodiments of the present invention, the second cutting blades 143d-1 may be detachably coupled in a fitted manner to facilitate replacement. This is to maintain clean hygiene at the time of separation of the follicles of the next patient by replacing when the follicles are separated after the clean cutting is not made due to damage or wear of the cutting blade.

The follicle position sensor 143d-2 detects the position and direction of the follicles before the second cutting hydraulic cylinder moves down and sets the secondary position and rotation angle of the second cutting rotary unit, whereby the follicle damage can be minimized by the second cutting blade to maximize the engraftment rate of follicles.

Follicle selective unit 150 is cut in the form of follicles to the bottom of the frame of the "⊏" shape rotated 90 degrees clockwise formed upright to the rear end direction of the second cutting unit 140 to the left of the conveyor belt travel direction. Each follicle is picked up, transported in a vertical direction, and selected and classified according to the number of hairs formed in the separated units of follicles.

Figure 17:
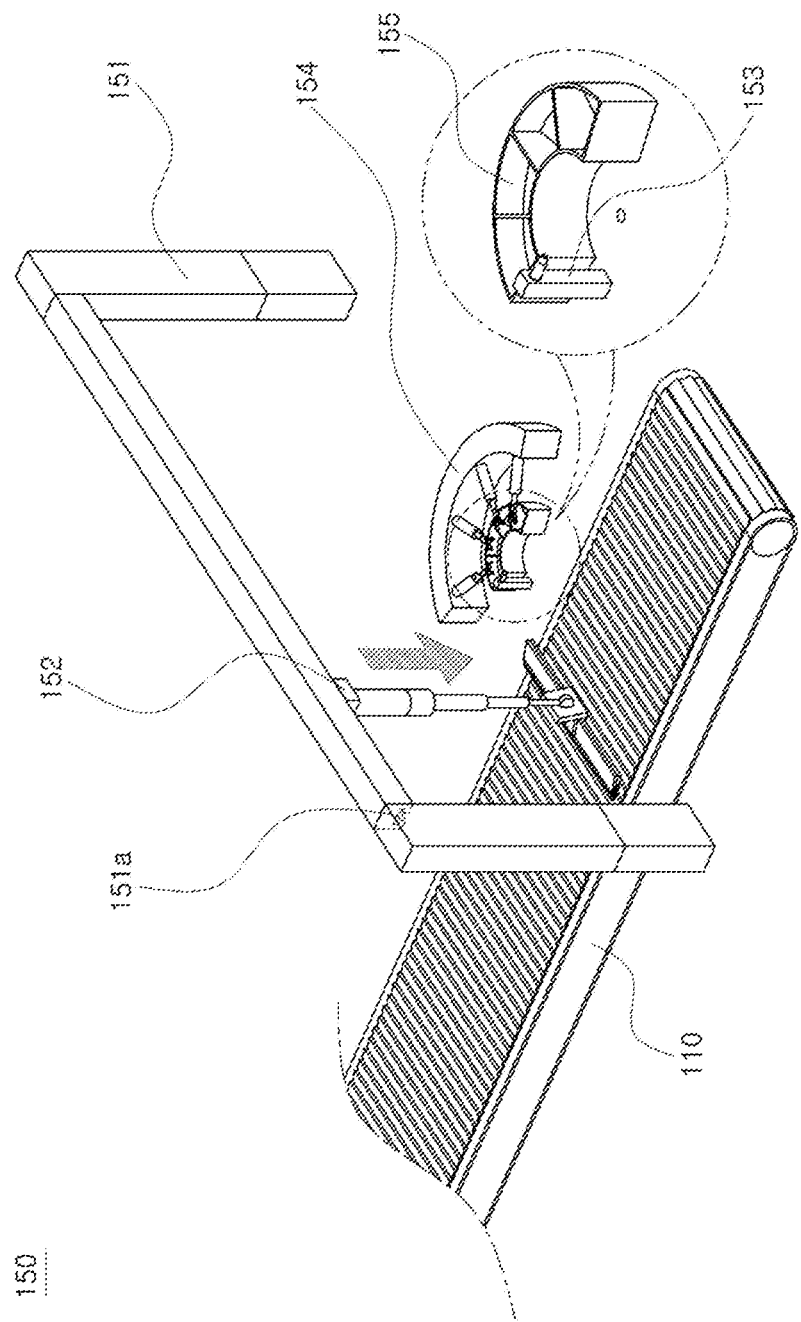
FIG. 17 is a perspective view of a follicle selecting unit according to some embodiments of the present invention.

As shown in FIG. 17, the follicle selective unit 150 includes a selective support 151, a follicle selective transporting unit 152, a follicle selective sensor 153, a follicle selective pincer 154, and a follicle storing unit 155.

The selective transporting support 151 is a "⊏" shaped frame rotated 90 degrees clockwise across the top of the conveyor belt in a vertical direction, and a vertical guide rail 151a is formed to support a reciprocate vertically.

Figure 18:
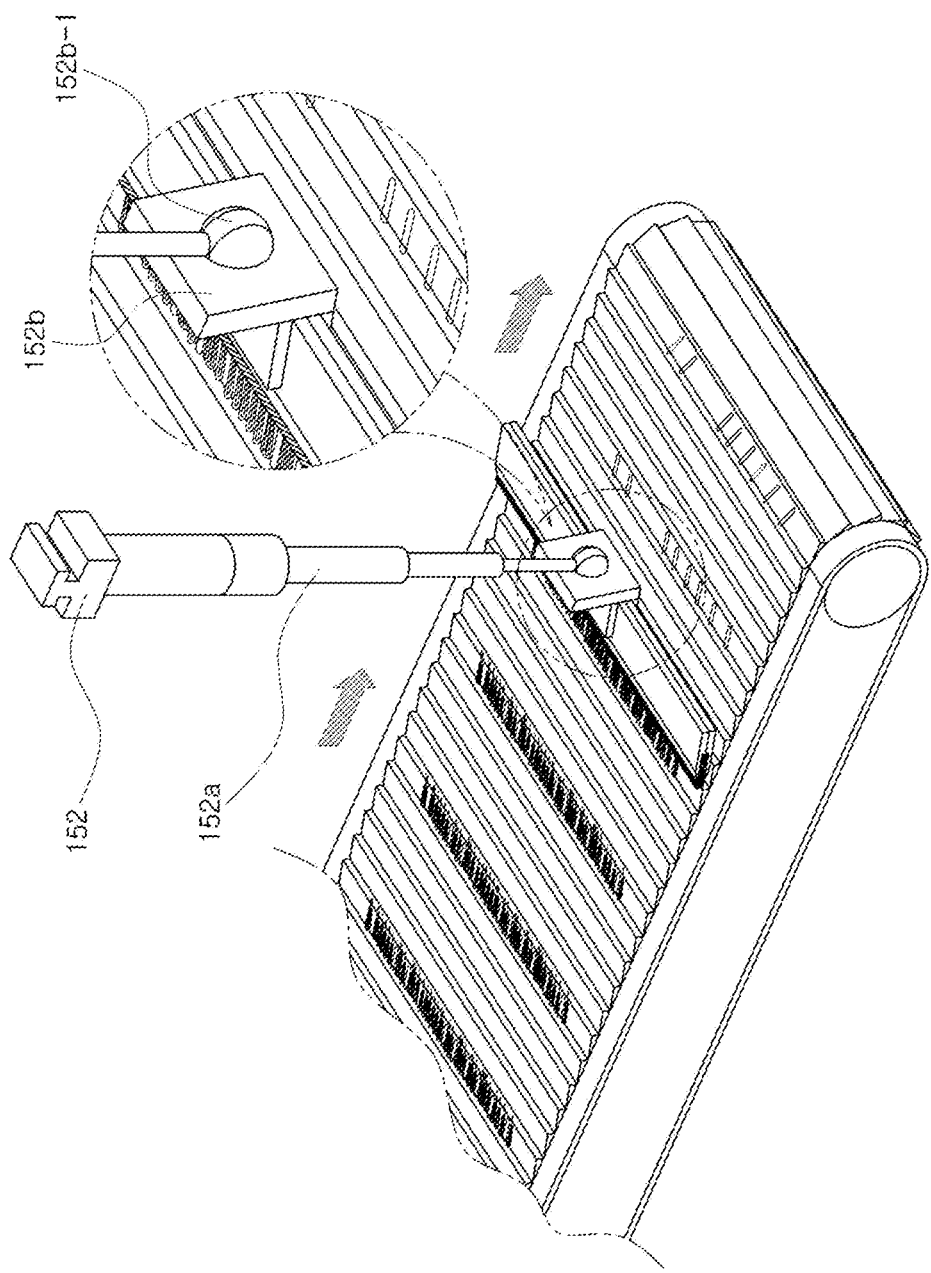
FIG. 18 is a perspective view of a selective follicle transporting unit according to some embodiments of the present invention.

As shown in FIG. 18, the follicle selective transporting unit 152 has a cylindrical shape coupled to the vertical guide rail 151a of the selective transporting support 151 at the top thereof, is reciprocated in the vertical direction and supports the follicle selective hydraulic cylinder 152a and the follicle selective transporting frame 152b coupled in the lower direction.

The follicle selective hydraulic cylinder 152a has a cylindrical shape coupled to the lower end of the follicle selective transporting unit 152, and the follicle selective transporting frame 152b is coupled to the lower end thereof, and the connective tissue in the form of slices cut in units of follicles is cut in the lower direction. The position of the follicle selective transporting frame 152b is controlled by moving up and down depending on whether it is the skin tissue is positioned.

As shown in FIG. 19, the follicle selective transporting frame 152b has a semicircular vertical rotary unit 152b-1 shaft-coupled to the lower end of the follicle selective hydraulic cylinder 152a, and has a rectangular plate shaped frame formed in front of the vertical rotary unit, and a follicle bottom support frame 152b-2 and a follicle top support frame 152b-3 having the same length as the width of the conveyor belt in the front surface vertical direction of the frame.

Figure 20:
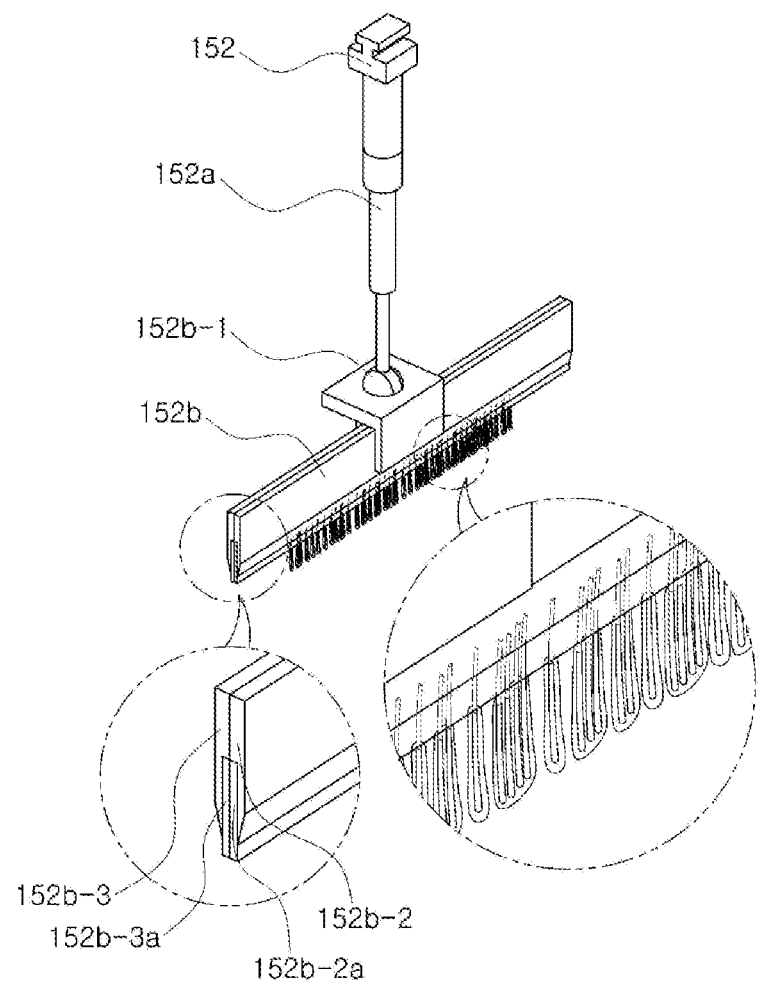
FIG. 20 is a perspective view of a selective follicle transporting unit according to some embodiments of the present invention.

At this time, the follicle bottom support frame 152b-2 is made of a support frame, as shown in FIG. 20, and the follicle top support frame 152b-3 is formed in a movable form capable of reciprocating in the vertical direction, and the follicle supporting top silicon 152b-3a is formed on the front lower surface in the longitudinal direction.

As shown in FIG. 20, the follicle bottom support frame 152b-2 is positioned at the bottom of the sawtooth pattern of the antibacterial cutting plate 111 of the conveyor belt so that when the hair of the separated follicles is placed on the follicle support bottom silicon 152b-2a, the follicle support top silicon 152b-3a is engaged with the follicle support bottom silicon 152b-2a with the follicle support bottom silicon 152b-2a lowered vertically to pick up hair separated in units of follicles positioned therebetween.

Thereafter, the follicle selective hydraulic cylinder 152a is raised, and the vertical rotary unit 152b-1 is rotated so that the follicle selective transporting unit 152 moves in the vertical direction along the vertical guide rail 151a.

The follicle support top silicon 152b-3a and the follicle support bottom silicon 152b-2a are made of a material having frictional force and elasticity and having antibacterial properties.

This prevents the hair of the separated unit of follicles from being exposed to bacteria or strongly picked up and damaged by bending, and prevents the hair from sliding down and falling down.

The follicle selective sensor 153 is formed so as to match the height of the units of follicles picked up during vertical movement of the follicle selective transporting unit, and detects the number of hairs formed in each of the separate units of follicles passing through the front direction to transport to the follicle separation control unit 20.

Figure 21:
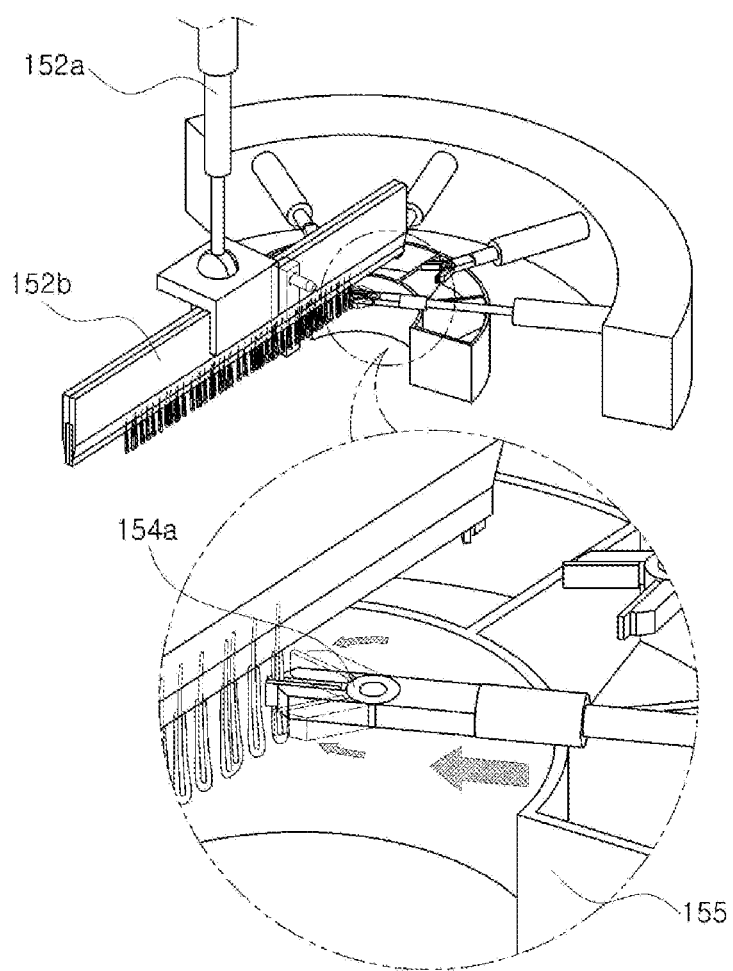
FIG. 21 is a perspective view of a selective follicle transporting unit and a selective follicle pincer according to some embodiments of the present invention.
Figure 22:
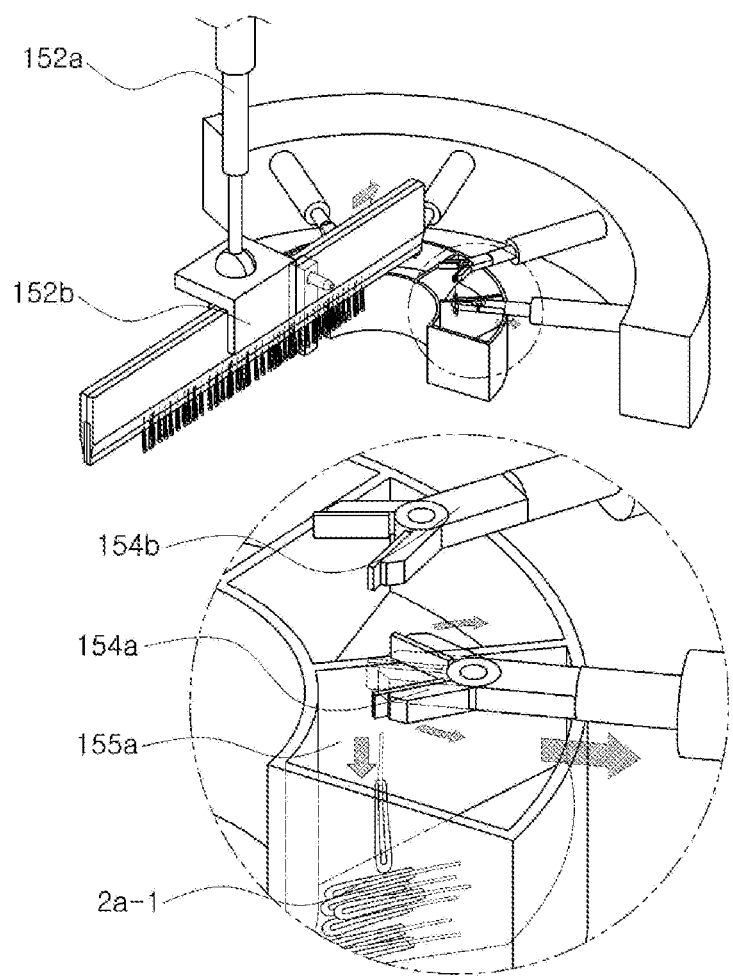
FIG. 22 is a perspective view of a selective follicle pincer and a first follicle storing unit according to some embodiments of the present invention.
Figure 23:
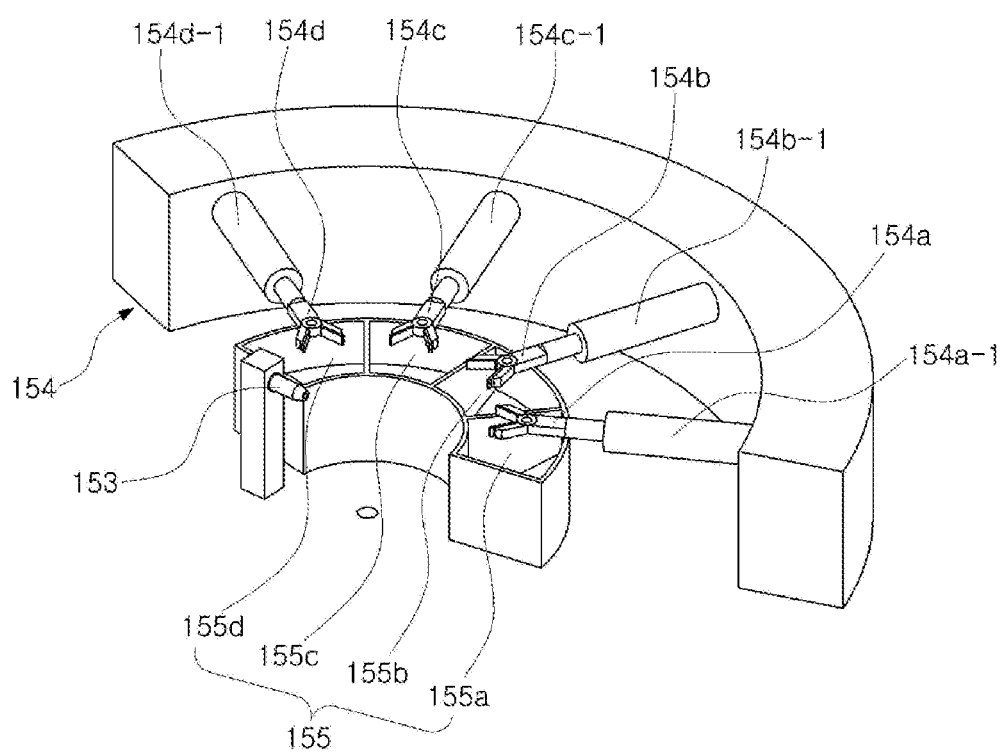
FIG. 23 is a perspective view of a selective follicle pincer and a first follicle storing unit according to some embodiments of the present invention.

As shown in FIGS. 21-23, when the number of hairs formed in the unit of follicles passing through is one, the first follicle selective pincer 154a is moved and the hair is picked up so as to be stored in the first follicle storage groove 155a. When the number of hairs formed in the units of follicles passing through is two, the second follicle selective pincer 154b is moved and the hairs are picked up to be stored in the second follicle storage groove 155b. When the number of hairs formed in the units of follicles passing through is three, the third follicle selective pincer 154c is moved and the hairs are picked up to be stored in the third follicle storage groove 155c. When the number of hairs formed in the units of follicles passing through is four, the fourth follicle selective pincer 154d is moved and the hairs are picked up to be stored in the fourth follicle storage groove 155d.

This enables classification according to the number of hairs formed in the units of follicles to be provided to the doctor.

The follicle selective pincer 154 has a shape in which four pincers protrude from the inner surface of the semi-arc frame-shaped support at regular intervals on the inner side of the semi-arc frame-shaped support, which is picked up by the follicle selective transporting unit 152. The follicle selective pincer 154 is selected according to the number of hairs formed in the units of follicles passing through the follicle selective sensor.

As shown in FIGS. 20 to 22, the follicle selective pincer 154 includes a first selective follicle pincer 154a, a second follicle selective pincer 154b, a third follicle selective pincer 154c, and a fourth follicle selective pincer 154d.

First follicle selective pincer 154a is formed in the right direction with respect to the center point of the semi-arc support, the silicon material is coupled to the left and right sides of the front pincers of the pincers to have an structure that opens and closes according to rotation, and a first pincer hydraulic cylinder 154a-1 is formed at the rear of the pincers to reciprocate in the front-rear direction.

When the number of hairs formed in the unit of follicles passing through the front of the follicle selective sensor 153 is one, the first pincer hydraulic cylinder 154a-1 is moved forward, and a front pincer of the first follicle selective pincer 154a closes on a follicle formed having one hair positioned at the center of a semi-arc type support to pick up the hair and separate it from the follicle selective transporting unit, and then the first follicle selective pincer 154a returns to the rear and the front pincer opens for storing in the first follicle storage groove 155a positioned at the bottom.

The second follicle selective pincer 154b are formed on the left side of the first selective follicle pincer based on the center of the semi-arc support, and the silicon material is coupled to the left and right sides of the front pincer surface to open and close the pincer according to rotation. The second pincer hydraulic cylinder 154b-1 is formed at the rear of the pincer and reciprocates in the front-rear direction.

When the number of hairs formed in the units of follicles passing through the front of the follicle selection sensor 153 is two, the second pincer hydraulic cylinder 154b-1 is moved forward and a front pincer of the second follicle selective pincer 154b closes on a follicle formed having two hairs positioned at the center of a semi-arc type support to pick up the hair and separate it from the follicle selective transporting unit, and then the second follicle selective pincer 154b returns to the rear and the front pincer opens for storing in the second follicle storage groove 155b positioned at the bottom.

The third follicle selective pincer 154c are formed on the left side of the second selective follicle pincer based on the center point of the semi-arc support, and the silicon material is coupled to the left and right sides of the front pincers to open and close the pincers according to rotation. The third pincer hydraulic cylinder 154c-1 is formed at the rear of the pincer and reciprocates in the front-rear direction.

When the number of hairs formed in the units of follicles passing through the front of the follicle selective sensor 153 is three, the third pincer hydraulic cylinder 154c-1 is moved forward and a front pincer of the third follicle selective pincer 154c closes on a follicle formed having three hairs positioned at the center of a semi-arc type support to pick up the hair and separate it from the follicle selective transporting unit, and then the third follicle selective pincer 154c returns to the rear and the front pincer opens for storing in the third follicle storage groove 155c positioned at the bottom.

The fourth follicle selective pincer 154d is formed on the left side of the third selective follicle pincer based on the center point of the semi-arc support. The fourth pincer hydraulic cylinder 154d-1 is formed to the rear of the pincer and reciprocates in the front-rear direction.

When the number of hairs formed in the units of follicles passing through the front of the follicle selection sensor 153 is four, the fourth pincer hydraulic cylinder 154d-1 is moved forward and a front pincer of the fourth follicle selective pincer 154d closes on a follicle formed having four hairs positioned at the center of a semi-arc type support to pick up the hair and separate it from the follicle selective transporting unit, and then the fourth follicle selective pincer 154c returns to the rear and the front pincer opens for storing in the fourth follicle storage groove 155d positioned at the bottom.

The follicle storing unit 155 has a semi-arc frame shape formed inside the follicle selective pincer 154, and a storage groove is formed at the bottom of each pincers of the follicle selective pincers, and partition walls are formed at regular intervals between the pincers. An inclined surface is formed to an inner portion of each storage groove.

A first follicle storage groove 155a inclined to the inner portion at the bottom of the first selective follicle pincer 154a is formed, and a second follicle storage groove 155b inclined to the inner portion at the bottom of the second follicle selective pincer 154b is formed, a third follicle storage groove 155c inclined to the inner portion at the bottom of the third follicle selective pincer 154c is formed, and a fourth follicle storage groove 155d inclined to the inner portion at the bottom of the fourth follicle selective pincer 154d is formed.

The problem of a lowered engraftment rate can be prevented by laying down a gauze moistened with physiological saline and placing the separated follicles on the follicles when the separated follicles are dried or blown onto the saline at each follicle storage groove.

In addition, the bottom surface of each follicle storage groove is made of an inclined surface to prevent the mixed follicles falling to the bottom by the selective follicle pincers to be mixed irregularly and fall in a certain direction so that the doctor can use without a separate procedure for selecting follicles, thereby saving preparation time for surgery.

The non-incisional follicle separating unit 200 cuts and separates the connective tissue attached to the lateral part of the units of follicles, which is extracted directly from the back of the head of an alopecic patient, in units of follicles, and according to the number of hairs included in the units of follicles, the selecting is performed individually and the non-incisional follicle separating unit includes the conveyor belt 110, the first cutting unit 140, and the follicle selective unit 150.

The non-incisional follicle separating unit 200 positions the follicles and connective tissues extracted from the patient in one row at the rear end of the first cutting unit 130 in the advancing direction of the conveyor belt unit, and the second cutting unit 140 and the follicle selective unit 150 separates the hair follicle and the connective tissue in the same driving order as the incisional follicle separation device.

The non-incisional follicle separating unit 200 may be used in a state where the scalp data analyzing unit 120 and the first cutting unit 130 are turned off in the incisional follicle separating unit 100, or the scalp data analyzing unit 120 and the first cutting unit 130 may be removed so as to use the non-incisional follicle separating unit 200 in a compact form in which the length of the follicle separating unit 10 is reduced.

When using the scalp data analyzing unit 120 and the first cutting unit 130 in the OFF state, it is possible to use a combination of incisional follicle separation and non-incisional follicle separation.

When the scalp data analyzing unit 120 and the first cutting unit 130 are removed, the overall length of the non-incisional follicle separation device can be reduced, and the components of the device can be reduced to reduce the manufacturing cost of the device.

The follicle separation control unit 20 converts the scanned scalp image information and numerical values into data and displays them on the display of the monitor unit and controls operation by adjusting setting values such as reaction speed and moving speed of separation device.

Hereinafter, a description will be given of the specific operation process of the incision follicle separation unit in the automatic hair-follicle separating apparatus according to at least one embodiment of the present invention.

First, the scalp tissue extracted from the patient is placed in the center of the front upper part of the conveyor belt.

Next, the conveyor belt unit rotates and the scalp tissue is advanced, and when the conveyor belt unit is positioned at the lower end of the scanning unit, the rotation of the conveyor belt unit stops.

At this time, the skin hardness measurement pin of the skin hardness measurement unit moves to the x, y axis to position and then descends in the vertical direction to measure the scalp hardness by measuring the pressure passing through the scalp tissue.

Next, the conveyor belt unit rotates to position the scalp tissue at the lower end of the first cutting scanning unit, and then rotation is stopped. The front pin fixing bar and the rear pin fixing bar of the pin fixing unit are positioned at the front and the rear and then the front left and right pins, and the pin and the rear left and right pins descend to fix the scalp tissue.

Next, the first cutting blade support is located in front of the front pin fixing bar and the first cutting rotary unit is gradually rotated in the vertical lower direction, the first cutting hydraulic cylinder is reciprocated and the first cutting blade is moved to move forward one side of the skin tissue.

Next, the conveyor belt unit is rotated to position the connective tissue in the form of slice at the lower end of the second cutting scanning unit, and the rotation is stopped, and the follicle formed in the connective tissue in the form of slice is formed through the second cutting scanning unit and the follicle position sensor. After detecting the position and direction, the second cutting rotation part is rotated to position the second cutting blade in the lateral vertical direction of the follicle, and then lowered to cut the left and right sides of the follicle without damaging the follicle, thereby separating the connective tissue and each follicle.

Next, the conveyor belt unit is rotated to position the hair formed on the top of the follicles in the follicle support bottom silicon located in the follicle bottom support frame of the follicle selective transporting unit, and then the follicle support bottom silicon is lowered by lowering the follicle support bottom silicon. Then the separated follicles are placed in between and are moved up.

Next, the follicle selective transporting unit is stopped in front of the follicle selective sensor through a vertical guide rail, and at this time, the follicle selective pincers are selectively operated according to the number of hairs included in the follicles detected by the follicle selective sensor.

In this case, when the number of hairs contained in the follicles is one, the follicle selection first pincers are driven and inserted into the first follicle storage groove, and when the number of hairs included in the follicles is two, the follicles selection second pincers is driven and inserted into the second follicle storage groove. When the number of hairs inserted into the follicle storage groove, and the number of hair contained in the follicles is three, the follicle selection third pincers are driven and inserted into the third follicle storage groove, and when the number of hairs contained in the follicles is four, the follicle selection fourth pincers is driven and inserted into the fourth follicle storage groove.

Finally, by delivering undamaged healthy follicles selected and inserted into the follicle reservoir to the doctor for rapid hair transplantation, the engraftment rate of follicles planted in the scalp of the patient can be improved.

Hereinafter, a detailed operation process of the non-incisional follicle separation unit in the automatic hair-follicle separating apparatus according to at least one embodiment of the present invention will be described.

First, the connective tissue including the units of follicles pulled out directly from the back of the hair loss patient is placed in a single row so that the hair faces rearward in the center of the upper part of the conveyor belt of the front part of the second cutting device.

Next, when the connective tissue including the units of follicles arranged in a row at the bottom of the second cutting scanning unit is rotated by rotating the conveyor belt unit, the rotation is stopped, and the position of the follicle is detected through the second cutting scanning unit and the follicle position sensor. After detecting the direction, the second cutting rotary unit is rotated to position the second cutting blade in the lateral vertical direction of the follicles, and then descends to cut the left and right sides of the follicles without damaging the follicles to separate the connective tissue and each follicle.

Next, the conveyor belt unit is rotated to position the hair protruding in the upper direction of the follicles in the follicle support lower silicon located in the follicle bottom support frame of the follicle selective transporting unit, and then the follicle support lower silicon is lowered to support the follicle support lower silicon and the follicle support. Place separate follicles between the top silicon to be picked up and raise them.

Next, the follicle selective transporting unit is stopped by positioning the follicle selective sensor forward through the vertical guide rail, and at this time, selectively operates the follicle selective pincers according to the number of hairs included in the units of follicles detected by the follicle selective sensor.

In this case, when the number of hairs included in the units of follicles is one, the follicle selection first pincers are driven and inserted into the first follicle storage groove. When the number of hairs included in the units of follicles is two, the follicle selection second pincers are driven and inserted into the second follicle storage groove. When the number of hairs included in the units of follicles is three, the follicle selection third pincers are driven and inserted into the third follicle storage groove. When the number of hairs included in the units of follicles is four, the follicle selection fourth pincers are driven and inserted into the fourth follicle storage groove.

Finally, by delivering undamaged healthy follicles selected and inserted into the follicle storing unit to the doctor for rapid hair transplantation, the engraftment rate of follicles planted in the scalp of the patient can be improved.

In an embodiment of the present invention, various sensors such as a skin tissue sensor, a follicle position sensor, a follicle selective sensor may be used by selecting an appropriate type of sensor from among sensors such as an optical sensor and an ultrasonic sensor however it is not limited thereto.

In the embodiment of the present invention, a blade-type cutting blade is used for cutting blades such as the first cutting blade and the second cutting blade, but the present invention is not limited thereto. For example, skin tissue may be cut using a waterjet or a laser, if necessary.

At least one embodiment of the present invention uses a conveyor belt as a means for transporting skin tissue, but the present invention is not limited thereto. For example, the sample plate may be moved in the front-rear direction by converting the rotational motion of the drive motor into a linear motion using a sample plate for placing skin tissue and a rack and pinion device.

In the embodiment of the present invention, the pin is moved up and down by using a hydraulic cylinder to the pin fixing portion for fixing the skin tissue on the conveyor belt, but the present invention is not limited thereto. For example, a pin or a solenoid device may be used to move the pin up and down as needed.

The present invention should not be limited to the above-mentioned embodiments but various changes and modifications can be made by a person having ordinarily skill in the art within the subject matter, the spirit and scope of the present invention as hereinafter claimed. Specific terms in the specification and drawings are used for illustrative purposes and not to be considered as limitations of the present invention. Exemplary embodiments of the present invention have been described for the sake of brevity and clarity. Accordingly, a person having ordinary skill in the art would understand the scope of the claimed invention is not to be limited by the above-mentioned embodiments but by the claims and equivalents thereof.

What is claimed is:

1. An apparatus for determining defective hair follicles, the apparatus comprising:
    an image acquiring unit configured to acquire an image of a follicle and a hair included in the follicle for each follicle separated from a scalp cut from back of a head of an alopecic patient in an incisional hair transplant or each follicle directly extracted from back of a head of an alopecic patient in a non-incisional hair transplant;
    an image processing unit configured to extract an outline pattern of the image of the follicle and the hair by performing a contour detection process or an edge detection process on the image of the follicle and the hair acquired by the image acquiring unit;
    a follicle shape database configured to store hair pixel patterns related to various shapes of hairs and follicle pixel patterns related to various shapes of follicles; and
    a follicle determining unit configured to determine whether a follicle is a normal follicle or a defective follicle by comparing the outline pattern of the image of the follicle and the hair with the hair pixel patterns and follicle pixel patterns stored in the follicle shape database,
    wherein
        the follicle determining unit is configured to obtain a final image of the hair and the follicle by comparing the outline pattern of the image of the hair and the follicle with the hair pixel patterns and the follicle pixel patterns stored in the follicle shape database, to set an outline of the final image of the follicle as an interest area, to build pixel coordinates by spatially dividing the interest area, to extract an outline area in the interest area, and to count the number of pixels for each line in the outline area.

2. The apparatus according to claim 1, wherein the follicle determining unit is configured to count a number of pixels in the image of the follicle and to determine whether the follicle is a normal follicle or a defective follicle by comparing the number of pixels counted with a number of reference pixels forming a shape of the follicle.

3. The apparatus according to claim 2, further comprising a display unit, wherein
    the follicle determining unit is configured to calculate a percentage of the number of pixels counted to the number of reference pixels and to output the image of the follicle and the percentage to the display unit.

4. The apparatus according to claim 1, wherein the image processing unit is configured to convert the image of the hair and the follicle acquired by the image acquiring unit into a grayscale image, to remove a noise signal included in the grayscale image, to extract edges of the hair and the follicle from the grayscale image by performing an image processing including a contour detection process or an edge detection process, and to set images of the hair and the follicle to black with a pixel value of zero and a background other than the hair and the follicle to white with a pixel value of 255.

5. The follicle identifying device according to claim 1, wherein
    the follicle shape database is further configured to store an outline shape of a reference follicle corresponding to a width of a follicle and the number of reference pixels forming a shape of the corresponding follicle, and
    the follicle determining unit is configured to draw a plurality of horizontal imaginary lines in a horizontal direction and a plurality of vertical imaginary lines in a vertical direction on black pixels at a plurality of positions in the outline area, to calculate a distance between black pixels using pixel coordinates on each horizontal imaginary line and pixel coordinates on each vertical imaginary line, to set a maximum distance among distance between the black pixels as a width of the outline area representing a follicle area, to search a shape of a follicle and a number of reference pixels corresponding to the width of the outline area, to calculate a percentage of the number of pixels counted to the number of reference pixels searched, to determine whether the percentage is equal to or more than a predetermined percentage of a normal follicle or not, if the percentage is equal to or more than the predetermined percentage of normal follicle, to determine that the follicle is a normal follicle, and if the percentage is less than the predetermined percentage of normal follicle, to determine that the follicle is a defective follicle.

6. The apparatus according to claim 1, wherein
    the follicle shape database is further configured to store an outline shape of a reference follicle, a pixel pattern of the reference follicle, and a number of reference pixels related to the shape of the follicle, and
    the follicle determining unit is configured to compare the pixel pattern forming the outline pattern with the pixel pattern of the reference follicle stored in the follicle shape database to count the number of pixels for each line in the outline area, to calculate a percentage of the number of pixels counted to the number of reference pixels, to determine whether the percentage is equal to or more than a predetermined percentage of normal follicle or not, if the percentage is equal to or more than the predetermined percentage of normal follicle, to determine that the follicle is a normal follicle, and if the percentage is less than the predetermined percentage of normal follicle, to determine that the follicle is a defective follicle.

7. The apparatus according to claim 5, wherein the follicle determining unit is configured to change the predetermined percentage of normal follicle, to determine whether the percentage is equal to or more than a changed percentage of normal follicle or not, if the percentage is equal to or more than a changed percentage of normal follicle, to determine that the follicle is a normal follicle, and if the percentage is less than the changed percentage of normal follicle, to determine that the follicle is a defective follicle.

8. The apparatus according to claim 6, wherein the follicle determining unit is configured to change the predetermined percentage of normal follicle, to determine whether the percentage is equal to or more than a changed percentage of normal follicle or not, if the percentage is equal to or more than a changed percentage of normal follicle, to determine that the follicle is a normal follicle, and if the percentage is less than the changed percentage of normal follicle, to determine that the follicle is a defective follicle.

9. An apparatus for automatically separating hair follicles, the apparatus comprising:

a follicle separating unit including a defective hair follicle determining device and configured
to cut a skin tissue of a scalp cut from a back of a head of an alopecic patient in units of follicles and to classify follicles by a number of hairs included in each follicle in an incisional hair transplant, or
to classify follicles each directly extracted from the back of the head of the alopecic patient by the number of hairs included in each follicle in a non-incisional hair transplant; and
a follicle separation control unit configured to control an operation of the follicle separating unit, wherein
the defective hair follicle determining device includes
an image acquiring unit configured to acquire an image of a follicle and a hair included in the follicle for each follicle separated from a scalp cut from back of a head of an alopecic patient in an incisional hair transplant or each follicle directly extracted from back of a head of an alopecic patient in a non-incisional hair transplant,
an image processing unit configured to extract an outline pattern of the image of the follicle and the hair by performing a contour detection process or an edge detection process on the image of the follicle and the hair acquired by the image acquiring unit,
a follicle shape database configured to store hair pixel patterns related to various shapes of hairs and follicle pixel patterns related to various shapes of follicles, and
a follicle determining unit configured to determine whether a follicle is a normal follicle or a defective follicle by comparing the outline pattern of the image of the follicle and the hair with the hair pixel patterns and follicle pixel patterns stored in the follicle shape database, and
the follicle determining unit is configured to obtain a final image of the hair and the follicle by comparing the outline pattern of the image of the hair and the follicle with the hair pixel patterns and the follicle pixel patterns stored in the follicle shape database, to set an outline of the final image of the follicle as an interest area, to build pixel coordinates by spatially dividing the interest area, to extract an outline area in the interest area, and to count the number of pixels for each line in the outline area.

10. The apparatus according to claim 9, wherein the follicle determining unit is configured to count a number of pixels in the image of the follicle and to determine whether the follicle is a normal follicle or a defective follicle by comparing the number of pixels counted with a number of reference pixels forming a shape of the follicle.

11. The apparatus according to claim 10, further comprising a display unit, wherein
the follicle determining unit is configured to calculate a percentage of the number of pixels counted to the number of reference pixels and to output the image of the follicle and the percentage to the display unit.

12. The apparatus according to claim 9, wherein the image processing unit is configured to convert the image of the hair and the follicle acquired by the image acquiring unit into a grayscale image, to remove a noise signal included in the grayscale image, to extract edges of the hair and the follicle from the grayscale image by performing an image processing including a contour detection process or an edge detection process, and to set images of the hair and the follicle to black with a pixel value of zero and a background other than the hair and the follicle to white with a pixel value of 255.

13. The apparatus according to claim 9, wherein
the follicle shape database is further configured to store an outline shape of a reference follicle corresponding to a width of a follicle and the number of reference pixels forming a shape of the corresponding follicle, and
the follicle determining unit is configured to draw a plurality of horizontal imaginary lines in a horizontal direction and a plurality of vertical imaginary lines in a vertical direction on black pixels at a plurality of positions in the outline area, to calculate a distance between black pixels using pixel coordinates on each horizontal imaginary line and pixel coordinates on each vertical imaginary line, to set a maximum distance among distance between the black pixels as a width of the outline area representing a follicle area, to search a shape of a follicle and a number of reference pixels corresponding to the width of the outline area, to calculate a percentage of the number of pixels counted to the number of reference pixels searched, to determine whether the percentage is equal to or more than a predetermined percentage of a normal follicle or not, if the percentage is equal to or more than the predetermined percentage of normal follicle, to determine that the follicle is a normal follicle, and if the percentage is less than the predetermined percentage of normal follicle, to determine that the follicle is a defective follicle.

14. The apparatus according to claim 9, wherein
the follicle shape database is further configured to store an outline shape of a reference follicle, a pixel pattern of the reference follicle, and a number of reference pixels related to the shape of the follicle, and
the follicle determining unit is configured to compare the pixel pattern forming the outline pattern with the pixel pattern of the reference follicle stored in the follicle shape database to count the number of pixels for each line in the outline area, to calculate a percentage of the number of pixels counted to the number of reference pixels, to determine whether the percentage is equal to or more than a predetermined percentage of normal follicle or not, if the percentage is equal to or more than the predetermined percentage of normal follicle, to determine that the follicle is a normal follicle, and if the percentage is less than the predetermined percentage of normal follicle, to determine that the follicle is a defective follicle.

15. The apparatus according to claim 13, wherein the follicle determining unit is configured to change the predetermined percentage of normal follicle, to determine whether the percentage is equal to or more than a changed percentage of normal follicle or not, if the percentage is equal to or more than a changed percentage of normal follicle, to determine that the follicle is a normal follicle, and if the percentage is less than the changed percentage of normal follicle, to determine that the follicle is a defective follicle.

16. The apparatus according to claim 14, wherein the follicle determining unit is configured to change the predetermined percentage of normal follicle, to determine whether the percentage is equal to or more than a changed percentage of normal follicle or not, if the percentage is equal to or more than a changed percentage of normal follicle, to determine that the follicle is a normal follicle, and if the percentage is less than the changed percentage of normal follicle, to determine that the follicle is a defective follicle.

17. An apparatus for determining defective hair follicles, the apparatus comprising:

an image acquiring unit configured to acquire an image of a follicle and a hair included in the follicle for each follicle separated from a scalp cut from back of a head of an alopecic patient in an incisional hair transplant or each follicle directly extracted from back of a head of an alopecic patient in a non-incisional hair transplant;

an image processing unit configured to extract an outline pattern of the image of the follicle and the hair by performing a contour detection process or an edge detection process on the image of the follicle and the hair acquired by the image acquiring unit;

a follicle shape database configured to store hair pixel patterns related to various shapes of hairs and follicle pixel patterns related to various shapes of follicles; and a follicle determining unit configured to determine whether a follicle is a normal follicle or a defective follicle by comparing the outline pattern of the image of the follicle and the hair with the hair pixel patterns and follicle pixel patterns stored in the follicle shape database, wherein the follicle shape database is further configured to store an outline shape of a reference follicle, a pixel pattern of the reference follicle, and a number of reference pixels related to the shape of the follicle, and the follicle determining unit is configured to compare the pixel pattern forming the outline pattern with the pixel pattern of the reference follicle stored in the follicle shape database to count the number of pixels for each line in the outline area, to calculate a percentage of the number of pixels counted to the number of reference pixels, to determine whether the percentage is equal to or more than a predetermined percentage of normal follicle or not, if the percentage is equal to or more than the predetermined percentage of normal follicle, to determine that the follicle is a normal follicle, and if the percentage is less than the predetermined percentage of normal follicle, to determine that the follicle is a defective follicle.

\* \* \* \* \*